(12) United States Patent
Glückstad

(10) Patent No.: US 9,259,741 B2
(45) Date of Patent: Feb. 16, 2016

(54) SYSTEM FOR SORTING MICROSCOPIC OBJECTS USING ELECTROMAGNETIC RADIATION

(71) Applicant: Danmarks Tekniske Universitet, Lyngby (DK)

(72) Inventor: Jesper Glückstad, Frederiksberg (DK)

(73) Assignee: Danmarks Tekniske Universitet, Lyngby (DK)

( * ) Notice: Subject to any disclaimer, the term of this patent is extended or adjusted under 35 U.S.C. 154(b) by 0 days.

(21) Appl. No.: 14/368,109

(22) PCT Filed: Dec. 28, 2012

(86) PCT No.: PCT/DK2012/050512
§ 371 (c)(1),
(2) Date: Jun. 23, 2014

(87) PCT Pub. No.: WO2013/097870
PCT Pub. Date: Jul. 4, 2013

(65) Prior Publication Data
US 2014/0367315 A1    Dec. 18, 2014

Related U.S. Application Data

(60) Provisional application No. 61/581,320, filed on Dec. 29, 2011.

(30) Foreign Application Priority Data

Dec. 29, 2011 (EP) ..................................... 11389501

(51) Int. Cl.
 *B03B 7/00* (2006.01)
 *G02B 21/32* (2006.01)
 (Continued)

(52) U.S. Cl.
 CPC ............. *B03B 7/00* (2013.01); *B01L 3/502761* (2013.01); *B01L 3/502776* (2013.01);
 (Continued)

(58) Field of Classification Search
 CPC ............. B07C 1/02; B07C 5/02; B07C 5/34; B07C 5/362; C12Q 1/04; C12Q 1/045; C12Q 1/10; C12Q 1/18; C12Q 1/34; B03B 7/00; G21K 1/006; G01N 15/00; G01N 15/1459; G01N 15/1484; G01N 2015/149; B01L 3/502761; B01L 3/502776; B01L 2400/043; B01L 2200/0668; G02B 21/32
 USPC ......................................... 209/44.2, 552, 638
 See application file for complete search history.

(56) References Cited

U.S. PATENT DOCUMENTS

2002/0181837 A1  12/2002  Wang et al.
2005/0121604 A1   6/2005  Mueth et al.
2006/0163119 A1   7/2006  Hirano et al.

FOREIGN PATENT DOCUMENTS

WO    WO 96/34307 A1   10/1996
WO    WO 03/034118 A1   4/2003
(Continued)

OTHER PUBLICATIONS

Hoi, S.K. et al., "Microfluidic sorting system based on optical force switching" Appl Phys B, 2009, pp. 859-865, vol. 97.
(Continued)

*Primary Examiner* — David H Bollinger
(74) *Attorney, Agent, or Firm* — Knobbe Martens Olson & Bear LLP

(57) ABSTRACT

There is presented a system 10,100 for sorting microscopic objects 76, 78, 80, where the system comprises a fluid channel 66 with an inlet 68 and an outlet 70, where the fluid channel is arranged for allowing the fluid flow to be laminar. The system furthermore comprises a detection system 52 which enables detecting microscopic objects in the fluid channel and furthermore enables determining their position. The system furthermore comprises a controller 67, such as a computer, which receives the positions and accordingly controls a source of light beams so as to "shoot" light beams towards selected microscopic objects so as to "push" them into a new position. The system thereby enables sorting the selected microscopic objects. In more specific embodiments, the detection system furthermore assigns different categories to different microscopic objects, so as to enable sorting based on multiple categories.

14 Claims, 8 Drawing Sheets

(51) Int. Cl.
*B01L 3/00* (2006.01)
*G21K 1/00* (2006.01)
*G01N 15/00* (2006.01)
*G01N 15/14* (2006.01)

(52) U.S. Cl.
CPC ........... *G01N 15/00* (2013.01); *G01N 15/1459* (2013.01); *G01N 15/1484* (2013.01); *G02B 21/32* (2013.01); *G21K 1/006* (2013.01); *B01L 2200/0668* (2013.01); *B01L 2400/043* (2013.01); *G01N 2015/149* (2013.01)

(56) References Cited

FOREIGN PATENT DOCUMENTS

| WO | WO 2004/113993 | A1 | 12/2004 |
| WO | WO 2005/096115 | A1 | 10/2005 |
| WO | WO 2006/078759 | A2 | 7/2006 |
| WO | WO 2006/097101 | A1 | 9/2006 |
| WO | WO 2007/147497 | A2 | 12/2007 |
| WO | WO 2008/088395 | A2 | 7/2008 |
| WO | WO 2009/036761 | A1 | 3/2009 |
| WO | WO 2010/144745 | A2 | 12/2010 |

OTHER PUBLICATIONS

Merenda, Fabrice et al., "Refractive multiple optical tweezers for parallel biochemical analysis in micro-fluidics" Proc. of SPIE, 2007, pp. 64830A1-64830A9, vol. 6483.

Perch-Nielsen, Ivan R. et al., "Real-time interactive 3D manipulation of particles viewed in two orthogonal observation planes" Optics Express, Apr. 18, 205, vol. 13, No. 8.

Ulriksen, Hans-Ulrik et al., "Independent trapping, manipulation and characterization by an all-optical biophotonics workstation" Journal of the European Optical Society, 2008, pp. 08034-1-08034-5, Rapid Publications 3.

Wang, Mark W. et al., "Microfluidic sorting of mammalian cells by optical force switching" Nature Biotechnology, Jan. 2005, pp. 83-87, vol. 23, No. 1.

Wang, Xiaolin et al., "Cell Sorting with Combined Optical Tweezers and Microfluidic Chip Technologies" 11$^{th}$ Int. Conf. Control Automation Robotics and Vision, Singapore, Dec. 7-10, 2010, pp. 201-206.

SYSTEM FOR SORTING MICROSCOPIC OBJECTS USING ELECTROMAGNETIC RADIATION

CROSS REFERENCE TO RELATED APPLICATIONS

This application is a U.S. National Phase Application of PCT International Application No. PCT/DK2012/050512, filed Dec. 28, 2012, designating the United States of America and published in the English language, which is an International Application of and claims the benefit of priority to European Patent Application No. 11389501.5, filed Dec. 29, 2011, and U.S. Provisional Application Ser. No. 61/581,320, Dec. 29, 2011. The disclosures of the above-referenced applications are hereby expressly incorporated by reference in their entireties.

FIELD OF THE INVENTION

The present invention relates to a system for sorting microscopic objects, and in particular to a system, method and use of such system for sorting microscopic objects using electromagnetic radiation.

BACKGROUND OF THE INVENTION

For many applications it would be advantageous to be able to sort microscopic objects in a time-efficient manner. As an example, sorting of cells so as to isolate Circulating Tumour Cells (CTCs), is mentioned.

The reference WO 2006/078759 A2 describes using a method and apparatus for selecting a specific fraction from a heterogeneous fluid-borne sample using optical gradient forces in a microfluidic or fluidic system are presented. Samples may range in size from a few nanometers to at least tens of micrometers, may be dispersed in any fluid medium, and may be sorted on the basis of size, shape, optical characteristics, charge, and other physical properties. The selection process involves passive transport through optical intensity field driven by flowing fluid, and so offers several advantages over competing techniques. These include continuous rather than batch-mode operation, continuous and dynamic tunability, operation over a wide range of samples, compactness, and low cost.

It would be advantageous to provide a system which is time-efficient.

Hence, an improved system would be advantageous, and in particular a more time-efficient and/or reliable system would be advantageous.

SUMMARY OF THE INVENTION

It is a further object of the present invention to provide an alternative to the prior art.

In particular, it may be seen as an object of the present invention to provide a system that solves the above mentioned problems of the prior art with being time-efficient.

Thus, the above described object and several other objects are intended to be obtained in a first aspect of the invention by providing a system for sorting microscopic objects comprising:
 a fluid channel comprising an inlet and an outlet, the fluid channel being dimensioned so as to allow a flow of fluid between the inlet and the outlet to be laminar,
 a detection system for determining a set of one or more positions of one or more microscopic objects in the fluid channel, wherein the detection system is arranged for determining the set of one or more positions of the one or more microscopic objects being suspended in the fluid channel,
 means for providing a plurality of electromagnetic radiation beams being independently spatially controllable and propagating into the fluid channel, and
 a controller arranged for
   obtaining the set of one or more positions from the detection system, and
   control the plurality of electromagnetic radiation beams based on the set of one or more positions, so as to enable each of the electromagnetic radiation beams in the plurality of electromagnetic radiation beams to exert a force on a microscopic object within the one or more microscopic objects,
  wherein the force has a direction having a component being parallel with a primary axis, wherein the primary axis is parallel with the electromagnetic radiation beam and orthogonal to a direction of the flow of fluid, so as to enable sorting of the microscopic objects by displacing them spatially along the primary axis.

The invention may be particularly, but not exclusively, advantageous for obtaining a system capable of sorting microscopic objects in a time-efficient manner.

By 'microscopic object' is understood an object of microscopic dimensions, such as particles, beads or micro devices having lengths, width and height within a range from 1 nanometer to 1 millimeter, such as within a range from 1 nanometer to 100 micrometers, such as within a range from 1 nanometer to 10 micrometers, such as within a range from 1 nanometer to 1 micrometer.

'Electromagnetic radiation' (EMR) is well-known in the art. EMR is understood to include various types of electromagnetic variation, such as various types corresponding to different wavelength ranges, such as radio waves, microwaves, infrared radiation, EMR in the visible region (which humans perceive or see as 'light'), ultraviolet radiation, X-rays and gamma rays. The term optical is to be understood as relating to light. EMR is also understood to include radiation from various sources, such as incandescent lamps, LASERs and antennas. It is commonly known in the art, that EMR may be quantized in the form of elementary particles known as photons. In the present application, the terms 'light' and 'optical' is used for exemplary purposes. It is understood, that where 'light' or 'optical' is used it is only used as an example of EMR, and the invention is understood to be applicable to also other wavelength intervals where reference is made to 'light' or 'optical'.

An advantage of the present system may be, that by controlling the plurality of EMR beams, so as to enable each of the EMR beams in the plurality of EMR beams to exert a force on a microscopic object, wherein the force has a direction having a component being parallel with the EMR beams and orthogonal to a direction of the flow of fluid, it may be possible to sort the microscopic objects by displacing them spatially along the primary axis in a time-efficient manner. One reason for the time-efficiency may be that by utilizing the optical scattering force, the microscopic objects may be moved relatively fast. Another reason for the time-efficiency may be that by utilizing multiple EMR beams, multiple microscopic objects may be moved, such as be moved simultaneously. Another reason for the time-efficiency may be that by utilizing multiple EMR beams which are independently spatially controllable, the individual EMR beam may be moved to a position corresponding to the microscopic object to be moved, which may be faster than moving the microscopic object, or waiting for the microscopic object to move to a certain position as a result of forces applied to the microscopic object, such as hydrodynamic forces (within a fluid flow), and/or gravitational forces. A basic insight of the invention may thus be described as the insight that microscopic objects may be moved relatively fast using the scattering force of independently steerable incident light beams (which moves the microscopic object in the direction of propagation of the light beam), and that this may be exploited when applied in a flow cell dimensioned so as to allow laminar flow.

A possible advantage of determining the positions of the microscopic objects while they are suspended in the fluid channel may be that the position can be determined immediately after the microscopic objects have entered the fluid channel, i.e., without waiting for the microscopic objects to settle at the bounding surfaces of the fluid channel, such as at the walls of the fluid channel, such as at the bottom or top of the fluid channel, such as due to gravitational forces or buoyancy. Another advantage may be that the microscopic objects may be fragile or sensitive, or may otherwise change characteristics once in contact with solid surfaces, so that the microscopic objects preferably must be kept suspended during sorting.

By 'suspended' is understood that the microscopic objects are kept in the fluid phase in the fluid channel, such as floating within the fluid channel, such as not being placed adjacent to, such as being in contact with, the outer walls of the fluid channel due to gravity or buoyancy. In particular embodiments, the fluid channel is understood to comprise a suspension, such as a fluid with suspended microscopic objects, where the microscopic objects would eventually, after a period of time, settle at the bottom of the fluid channel due to gravity (sedimentation) or settle at the top of the fluid channel due to buoyancy (creaming). In other particular embodiments, the fluid channel is understood to comprise a colloid, such as a colloidal suspension, such as a fluid with suspended microscopic objects, where the microscopic objects do settle, such as sediment, or otherwise fall out of solution.

By 'sorting microscopic objects' is understood a physical separation of one or more microscopic objects. The microscopic objects may be sorted by moving, such as isolating the microscopic objects of interest, or the opposite namely removing the microscopic objects which are not of interest. It is further understood, that in more advanced embodiments, sorting may include sorting into more than two groups, i.e., not only sorting into microscopic objects of interest and microscopic objects which are not of interest, but subdividing and sorting the microscopic into different groups.

By 'fluid channel' is understood a pathway for fluid, such as tubing, such as a hollow channel in a solid element, such as a channel bounded by walls.

By 'inlet' is understood an entrance, such as a throughgoing hole, through which fluid may enter the fluid channel.

By 'outlet' is understood an exit, such as a through-going hole, through which fluid may exit the fluid channel.

By 'dimensioned so as to allow a flow of fluid between the inlet and the outlet to be laminar' is understood that the shape and dimensions of the fluid channel is of such as character, that the fluid flow is laminar. By 'laminar' is understood that within the fluid flow, the fluid flows in parallel layers, with no disruption between the layers. I.e., if a microscopic object occupies a given place in the fluid flow, then the position of the object downstream is known in advance, since there is little or no chaotic turbulence which causes the microscopic object to move orthogonally to the flow in an unpredictable manner. An advantage of having a laminar flow may thus be, that once a microscopic object is moved to or kept at a certain position, then the position of the microscopic object downstream can be predicted. Thus, the laminar flow enables sorting of microscopic objects by grouping objects of interest within a certain region in the fluid channel.

By 'detection system' is understood a system capable of determining a set of one or more positions of one or more microscopic objects in the fluid channel. More particularly, the detection system is a system capable of determining the presence and position of a plurality of microscopic objects within the fluid channel.

In a more particular embodiment, the detection system is a system capable of determining the presence and position of a plurality of microscopic objects suspended in the fluid channel, such as freely suspended in the fluid channel, such as suspended in a flowing fluid in the fluid channel. The detection system may in particular embodiments be able to distinguish between different categories of microscopic objects, such as by distinguishing between objects according to drugresponse, size, optical properties, such as fluorescence, size, shape, morphology, charge, radioactivity and/or other properties, such as physical properties.

By 'position' is understood at least a position in a 1-dimensional (1D) space (such as an x-coordinate), such as a two-dimensional (2D) space (such as a set of corresponding x- and y-coordinates), such as a three-dimensional (3D) space (such as a set of corresponding x-, y-, and z-coordinates). The detection system may in a particular embodiment comprise a vision system which can identify microscopic objects placed in the fluid channel. In a more particular embodiment, the vision system may further be arranged for distinguishing between microscopic objects, so as to enable categorizing the microscopic objects.

By 'a set of one or more positions of one or more microscopic objects' is understood a set of positions, such as set of coordinates in a 1D, 2D or 3D space so that the position of each individual microscopic object within a set of microscopic objects, such as microscopic objects within a certain category of microscopic objects, is described by the set.

By 'means for providing a plurality of EMR beams being independently spatially controllable' is understood a source of multiple EMR beams, wherein the source is capable of spatially control the EMR beams such as spatially control the EMR beams so that the EMR beams are substantially parallel, such as parallel, while still being able to be moved in the plane being orthogonal to a direction of propagation, so as to be incident on microscopic objects in the fluid channel. In a particular embodiment, the EMR beams may be spatially controllable with a resolution of 10 microns, such as 1 micron, such as 100 nanometer, such as 10 nanometer, such as 1 nanometer. In a particular embodiment, a microscopic object may be targeted, i.e., specifically illuminated with EMR with a resolution of 10 microns, such as 1 micron, such as 100 nanometer, such as 10 nanometer, such as 1 nanometer. It is to be understood that a direction of propagation of the EMR beams has a component in a direction being orthogonal to the direction of flow in the fluid channel, such as the direction of propagation being substantially orthogonal to the direction of flow in the fluid channel, such as the direction of propagation being orthogonal to the direction of flow in the fluid channel.

In a particular embodiment, the 'means for providing a plurality of EMR beams being independently spatially controllable and propagating into the fluid channel' comprises an EMR source, such as a laser source, and a spatial EMR modulator.

By 'spatial EMR modulator' is understood a spatial light modulator (SLM) as is known in the art. It is understood that the spatial EMR modulator may be provided in a number of embodiments including embodiments with movable parts, such as one or more movable mirrors, or embodiments with spatially distributed and electrically addressable elements which change their properties in terms of optical path length, transmittance, and/or reflectivity upon activation.

According to some embodiments of the invention the spatial EMR modulator comprises a liquid crystal device.

By 'a controller' is understood a unit capable of receiving information corresponding to the set of one or more positions, and furthermore for controlling the plurality of EMR beams. In a particular embodiment, the controller is a unit comprising a processor. In another particular embodiment, the controller is embodied by a computer, such as personal computer. It may be understood, that the controller is arranged for automatically, such as without human intervention, controlling the plurality of EMR beams. The controller may be operationally interconnected with peripheral units, such as the means for providing a plurality of spatially controllable EMR beams, a diffractive optical element, such as a spatial light modulator and/or the detection system. An advantage of automatic controlling, such as by computer implemented controlling, may be that it possibly enables faster, cheaper, prolonged and/or more reliable sorting.

By 'control the plurality of EMR beams' is understood controlling the activation and/or spatial position of one or more EMR beams. In a particular embodiment, the EMR beams may be controlled in terms of any one of: activation (on/off), power (watt), focus depth (i.e., the depth of focus if any, i.e., position of focus with respect to an axis parallel with a direction of propagation), spatial position with respect to a first axis being orthogonal to a direction of propagation, spatial position with respect to a second axis being orthogonal to a direction of propagation the second axis being orthogonal to the first axis, time of activation (i.e., for how long time the light source or laser is 'on' when activated). It is understood, that in particular embodiments, the EMR beams may be controlled so as to move each of the microscopic objects (which are to be moved) a certain, well-defined and pre-determined distance, so as to enable controllably positioning a microscopic object at a certain position along the primary axis, and so as to enable controllably positioning another microscopic object at the same or another certain position along the primary axis. In a particular embodiment, the EMR beams may be controlled so as to be incident on microscopic objects during flow, i.e., where the microscopic objects are moving. In a particular embodiment, the moving microscopic objects may be moving while illuminated by a stationary EMR beam.

In a particular embodiment, the moving microscopic objects may be moving while illuminated by a moving EMR beam, such as the EMR beam being spatially controlled so as to move with a similar velocity (speed and direction) as the moving microscopic objects.

By 'to exert a force on a microscopic object within the one or more microscopic objects' is understood that the EMR beams may each exert a scattering force or radiation pressure on any object on which they are incident. For microscopic objects, the scattering force may be large enough to accelerate and move the objects. In other words, intense beams of light can be used to physically push the small microscopic objects in the direction of the propagation of the EMR beam.

According to some embodiments of the invention the spatial EMR modulator is configured for providing a modulated light beam having a substantially flat intensity profile but non-flat phase profile. In particular embodiments the spatial EMR modulator is configured for providing a phase-only modulation wherein only the phase varies across a spatial EMR modulator (i.e., non-flat phase-profile). In particular embodiments, all other optical characteristics are substantially constant across the modulator. In particular exemplary embodiments of the present invention the spatial light modulator is approximated by a phase-only modulation of an input laser beam in a discrete pixel matrix. Phase-only modulation allows the entire incoming beam power to be diffractively distributed between the stimulation points with minimal power loss.

According to some embodiments of the invention the spatial EMR modulator is configured for providing amplitude-only modulation.

According to some embodiments of the invention the spatial EMR modulator is configured for generating EMR having a substantially non-flat phase profile and/or a non-flat amplitude profile with respect to the EMR emitted from the EMR source.

According to some embodiments of the invention the spatial EMR modulator is configured for providing concurrent phase and amplitude modulation, such as by means of two spatial modulation-subunits arranged for allowing concurrent phase and amplitude modulation of the incoming beam.

It is noted that the spatial modulation of the EMR can be done by a spatial EMR modulator, such as described in the reference "Real-time interactive 3D manipulation of particles viewed in two orthogonal observation planes", Ivan R. Perch-Nielsen, Peter John Rodrigo, and Jesper Glückstad, 18 Apr. 2005/Vol. 13, No. 8/Optics Express 2852, the contents of which are hereby incorporated by reference. In general, the spatial modulation could be carried out with known spatial light modulators including Liquid Crystal SLMs (LC-SLMs), Micro Electro-Mechanical Systems SLMs (MEMS-SLMs), deformable mirror SLMs, Acousto-Optic SLMs (AO-SLMs), or any other type of SLM A light ray is mathematically described as a one-dimensional mathematical object. As such, a light ray intersects any surface which is not parallel to the light ray at a point.

A light beam may be described as one or more light rays. A light beam therefore intersects a surface which is not parallel to the beam at a plurality of points, one point for each light ray of the beam. Generally, a profile of the light beam refers to an optical characteristic (intensity, phase, frequency, brightness, hue, saturation, etc.) or a collection of optical characteristics of the locus of all such intersecting points. Typically, but not obligatorily, the profile of the light beam is measured at a planar surface which is substantially perpendicular to the propagation direction of the light.

The locus of points at which all light rays of the beam has the same phase is referred to as the wavefront of the beam. For a collimated light beam, for example, the wavefront is a plane perpendicular to the propagation direction of the light, and the light is said to have a planar wavefront.

Thus, the term "profile" is used to optically characterize the light beam at its intersection with a given surface, while the term "wavefront" is used to geometrically characterize a surface for a given phase.

A profile relating to a specific optical characteristic is referred to herein as a specific profile and is termed using the respective characteristic. Thus, the term "intensity profile" refers to the intensity of the locus of all the intersecting points, the term "phase profile" refers to the phase of the locus of all the intersecting points, the term "frequency profile" refers to the frequency of the locus of all the intersecting points, and so on. Similarly to the general profile function, a specific profile function can also be represented by a two-dimensional function.

The 'EMR source' is a source of EMR and may in particular embodiments be a coherent light source, such as a laser. For example, the EMR source can be a monochromatic laser light source or a combination of several monochromatic laser light sources. Lasers which are not strictly monochromatic are also contemplated. A super continuum light source is e.g. referred to as a 'white light laser'. When several lasers are employed, they can operate simultaneously or in a time-multiplexed manner. It is also contemplated to use a specific wavelength of electromagnetic trapping or EMR, such as 830 nm (which has the advantage that at this wavelength there may be less risk of damaging biological tissue), such as 488 nm, such as 633 nm (which corresponds to a typical HeNe laser), such as 532 nm, such as 1070 nm, such as 1064 nm (which corresponds to a typical ND:YAG laser), such as 532 nm, such as 1550 nm (which has the advantage that it is well suited for transmittance through optical fibers), such as 2 micron or higher.

The EMR may in some embodiments be directed towards the fluid channel by means of optics which may include free-space optics (e.g., an arrangement of lenses, microlens arrays, diffractive elements, etc.) and/or guiding optics (e.g., waveguides, optical fibers, fiber bundles, gradient-index (GRIN) fiber lenses, lens-relay endoscopes, etc.) and/or a Generalized Phase Contrast filter (for efficiently transforming phase modulations into intensity modulations).

In a particular embodiment, the portion of the wall of the fluid channel which is traversed by the EMR beams is transparent. In a particular embodiment, the portion of the wall of the fluid channel which is traversed by the EMR beams is substantially smooth, such as smooth, such as smooth on a scale comparable to the microscopic objects to be sorted, such as smooth on a scale comparable to the microscopic objects to the width of the EMR beams.

According to another embodiment there is provided a system, wherein the force is a scattering force, such as the force responsible for displacing the microscopic object being the scattering force, such as the force being substantially, such as exclusively, the scattering force. It may be understood that by utilizing the scattering force, the microscopic objects may be moved relatively fast, since the scattering force is relatively larger than forces applied from, e.g., conventional optical trapping. It is understood that each EMR beam may exert a scattering force, such as a radiation pressure on any object on which they are incident. For microscopic objects, the scattering force may be large enough to accelerate and move the objects. In other words, intense beams of light can be used to physically push the small microscopic objects in the direction of the propagation of the EMR beam.

According to another embodiment there is provided a system, wherein the means (42) for providing a plurality of electromagnetic radiation beams (31, 32) is arranged for providing a plurality of upper and lower electromagnetic radiation beams, wherein the upper and lower electromagnetic radiation beams are arranged so as to form counter propagating beams which may be controlled so as to exert the force on the microscopic objects, such as exerting a force in the primary direction or against the primary direction. An advantage of having counter propagating beams may be, that it enables effectively exerting a force on a microscopic object in both directions along the primary axis. This may be due to the fact, that each of the counter propagating beams may be exert a scattering force along the primary axis, the forces exerted from each beam being anti-parallel. Another possible advantage may be that a large operating volume may be provided, since the counter propagating beams may exert scattering forces along a large distance. Counter propagating beams are described in the reference "Independent trapping, manipulation and characterization by an all-optical biophotonics workstation", by H. U. Ulriksen et al., J. Europ. Opt. Soc. Rap. Public. 3, 08034 (2008) which is hereby incorporated in entirety by reference. In a specific embodiment, each or both of the counter propagating beams are non-divergent, such as not-focused. An advantage of this may be that the scattering force is substantially constant along the non-focused beam.

According to another embodiment, there is provided a system, wherein the fluid channel is dimensioned so that a flow of pure water at room temperature may have a Reynolds number below 4000, such as below 2500, such as below 2300, such as below 2100, such as below 2000, such as below 1750, such as below 1500, such as below 1000, such as below 500. In a particular embodiment, the Reynolds number is given at an approximate volumetric flow rate, such as 0.1 microliter/second, such as 1 microliter/second, such as 2 microliter/second, such as 5 microliter/second, such as 10 microliter/second, such as 15 microliter/second, such as 20 microliter/second, such as 50 microliter/second, such as 100 microliter/second, such as 200 microliter/second, such as 500 microliter/second, such as 1000 microliter/second. The Reynolds number is commonly known in the art. An advantage of having a low Reynolds number may be that fluid flowing at low Reynolds numbers undergo smooth laminar flow and therefore undergo no mixing since the fluid flow is laminar, such as predictable, such as non-turbulent, such as non-chaotic.

According to another embodiment, there is provided a system, wherein the means for providing a plurality of electromagnetic radiation beams comprises any one of: A Generalized Phase Contrast setup and diffractive optics.

In a particular embodiment, there is provided a system, wherein the means for providing a plurality of electromagnetic radiation beams comprises a Generalized Phase Contrast (GPC) setup, such as a set of components enabling utilizing a Generalized Phase Contrast approach. Generalized Phase Contrast is generally known in the art. It is contemplated to use any kind of GPC setup, including GPC (which is described in the reference WO1996/034307 which is hereby incorporated by reference in entirety), analog GPC (which is described in the reference WO2009/036761 A1 which is hereby incorporated by reference in entirety), Matched filtering GPC (which is described in the reference WO2007/147497 A1 which is hereby incorporated by reference in entirety), 3D-GPC (which is described in the reference WO2005/096115 which is hereby incorporated by reference in entirety), multi-filter GPC (which is described in the reference WO2004/113993 which is hereby incorporated by reference in entirety) and a MOEMS-platform (which is described in the reference WO2006/097101 A1 which is hereby incorporated by reference in entirety). An advantage of using GPC may be that it provides an effective platform for controlling multiple, such as numerous, EMR beams. Another advantage may be that it can be implemented without employing moving components. Another advantage may be that it is fast, and it is noted, that the response time of the system, based on a liquid crystal SLM with fast ferroelectric liquid crystal, is sub-millisecond. This enables spatially moving the EMR beams within time intervals which are as short as 0.5 milliseconds.

In a particular embodiment, there is provided a system, wherein the means for providing a plurality of electromagnetic radiation beams comprises any one of a diffractive optics (which is described in the reference WO2003/034118 A1 which is hereby incorporated by reference in entirety). In a particular embodiment, there is provided a system wherein the means for providing a plurality of EMR beams comprises a system for providing diffractive beam shaping, such as a system for diffractive optics, such as a system for Fourier holography, such as a system for Fresnel holography, such as a system for holographic optical scattering.

Advantages of employing diffractive optics may include compactness in the setup with few additional optical elements required.

According to another embodiment, there is provided a system, wherein the detection system is arranged for distinguishing between at least two different categories of microscopic objects, and for determining the set of one or more positions as a category specific set of one or more positions of one or more microscopic objects of a specific category in the fluid channel. The detection system may, according to this embodiment, be capable of distinguishing between different categories of microscopic objects, such as by distinguishing between objects according to drug-response, size, optical properties, such as fluorescence, size, shape, morphology, charge, radioactivity and/or other properties, such as physical properties. An advantage of this embodiment may be that it enables utilizing the system for identifying and sorting, such as isolating, microscopic objects according to their category. For example, the system may be used for obtaining objects of a certain size from a large population of objects wherein the sizes of the individual objects may be both larger and smaller than the microscopic objects of interest.

According to another embodiment, there is provided a system, wherein the detection system is arranged for distinguishing between at least two, such as at least 3, 4, 5, 6, 7, 8 or 9, different categories of microscopic objects, and for determining a plurality of sets of one or more positions, each corresponding to a category specific set of one or more positions of one or more microscopic objects of a specific category in the fluid channel. The detection system may, according to this embodiment, be capable of distinguishing between a plurality of different categories of microscopic objects. An advantage of this embodiment may be that it enables utilizing the system for identifying and sorting, such as isolating, microscopic objects according to their category, wherein the outcome may be a plurality of different groups of microscopic objects which are sorted according to their category. For example, the system may be used for obtaining a plurality of groups of microscopic objects, where each group comprises microscopic objects of a certain size, from a large population of objects wherein the sizes of the individual objects may span a large range of sizes.

According to a further embodiment, there is provided a system, wherein the system is arranged so as to enable sorting of the microscopic objects within different categories by displacing them spatially along the primary axis according to their category. According to this embodiment, the system may be arranged for distributing the microscopic objects along the primary axis depending on their category. An advantage of this may be that microscopic objects of a certain category may subsequently be obtained by selecting microscopic objects having a certain position with respect to the primary axis. For example, the microscopic objects may be categorized according to their size, and distributed along the primary axis at a position depending on their size. Subsequently, microscopic objects of a particular size may simply be obtained, e.g., as microscopic objects in a flow at a particular outlet position.

According to another embodiment, there is provided a system, wherein the system comprises a loop for enabling recirculation of the fluid. A potential advantage of recirculating the fluid may be that if the inlet fluid is recirculated, the system need not sort out all microscopic objects during the first passage, and this in turn lessens the requirements of the system in terms of yield and/or capacity. Another potential advantage may be that it enables double-checking. If the flow comprising the sorted microscopic objects of interest is recirculated, it might be advantageous, since it enables checking whether only microscopic objects of interest are present, and/or it enables continuously concentrating the fluid with microscopic objects of interest.

According to another embodiment, there is provided a system, wherein each of the electromagnetic radiation beams within the plurality of electromagnetic radiation beams is not being focused, such as being non-divergent. In a particular embodiment, there is provided a system, wherein each of the electromagnetic radiation beams within the plurality of electromagnetic radiation beams does not form an optical trap, such as an optical trap suitable for trapping a microscopic object.

According to another embodiment, there is provided a system, wherein each of the EMR beams within the plurality of EMR beams is non-divergent. By 'non-divergent' is understood an EMR beam which is composed of a plurality of light rays wherein the individual light rays are substantially parallel, such as parallel, such as parallel compared to the distance traversed through the fluid channel, such as not being focused, such as tightly focused, within the fluid channel, such as not being focused to a degree enabling trapping, such as three-dimensional (3D) trapping, of microscopic objects within the fluid channel. An advantage of having non-divergent EMR beams may be that it renders the need for focusing superfluous. Another potential advantage is that the scattering force of the EMR beam may be essentially constant and dominating over any potential gradient forces, such as constant throughout the depth of the fluid channel, which in turn renders the requirement of moving the focus superfluous. Another potential advantage is the presence of the catapulting effect of moving microscopic objects.

According to another embodiment, there is provided a system, wherein the controller is arranged for controlling the plurality of electromagnetic radiation beams based on the set of one or more positions, so as to enable each of the electromagnetic radiation beams in the plurality of electromagnetic radiation beams to exert a force on a microscopic object within the one or more microscopic objects, while the microscopic objects are suspended in the fluid channel. A possible advantage of this may be that it enables moving, such as catapulting, selected microscopic objects along the primary axis while they are suspended in the fluid channel. This may be advantageous for speeding up the sorting process and/or avoid that the microscopic objects touch the walls of the microfluidic channels (and/or each other) and/or it enables that both the microscopic objects which are moved along the primary axis and the remaining microscopic objects, which in turn enables that all microscopic objects may moved by the fluid flow in the fluid channel. The sorting process may thus be faster, since the catapulting of the microscopic objects may take place immediately after the positions and/or category of the microscopic objects have been determined by the detection system, i.e., without waiting for the microscopic objects to settle at the bounding surfaces of the fluid channel, such as at the walls of the fluid channel, such as at the bottom or top of the fluid channel, such as due to gravitational forces or buoyancy. Another advantage may be that the microscopic objects may be fragile or sensitive, or may otherwise change characteristics once in contact with solid surfaces, so that the microscopic objects preferably must be kept suspended during sorting.

According to another embodiment, there is provided a system, wherein the system furthermore comprises a pumping system for driving the fluid through the fluid channel. The pump may be any one of known pumps, including a syringe pump or a peristaltic pump. An advantage of having a pump may be that it enables controlling the flow and in particular the flow rate.

According to another embodiment, there is provided a system, wherein the pumping system is arranged for stopping and starting the flow depending on an operational status of the detection system and/or the controller. By 'operational status' of the detection system is to be understood the state of the detection system, and more specifically whether the detection system is in the process of obtaining information regarding the category and/or positions of the microscopic objects in the fluid channel. By 'operational status' of the controller is to be understood the state of the controller, and more specifically whether the controller is in the process of controlling the one or more EMR beams. A possible advantage of stopping and starting the flow, such as repeatedly stopping and starting the flow, contrary to a continuous flow, may be that whereas the flow rate might be relatively high, at least during limited periods of time, so as to move the microscopic objects fast, such as to move the microscopic objects fast in a direction of the fluid flow in the fluid channel, the flow rate may also be relatively low, such as completely stopped, during periods of time, so as to improve and/or simplify the task of the detection system of distinguishing between different categories of microscopic objects and/or determining positions. Similarly, the flow rate may at certain periods in time be reduced, such as completely stopped, so as to improve and/or simplify the task of the controller of controlling the plurality of EMR beams based on the set of one or more positions, so as to enable each of the EMR beams in the plurality of EMR beams to exert a force on a microscopic object within the one or more microscopic objects. In a specific embodiment, the flow is only stopped during a period of time being sufficient for obtaining an image of the microscopic objects in the fluid channel. In another specific embodiment, the flow is only stopped during a period of time being sufficient for moving microscopic objects in the fluid channel using the EMR beams, such as using the scattering force applied on the microscopic objects by the EMR beams, such as catapulting the microscopic objects. In another specific embodiment, the flow is stopped, during periods of time being less than 5 seconds, such as less than 2 seconds, such as less than 1 second, such as less than 0.5 second, such as less than 0.1 second, such as less than 0.05 second.

According to another embodiment, there is provided a system wherein the flow is non-zero during the time period in which the detection system is in the process of obtaining information regarding the category and/or positions of the microscopic objects in the fluid channel.

According to another embodiment, there is provided a system wherein flow is non-zero during the time period in which the controller is in the process of controlling the one or more EMR beams.

According to another embodiment, there is provided a system, wherein the fluid channel comprises a plurality of outlets distributed along the primary axis. The plurality of outlets may comprise any number of outlets, such as 2, 3, 4, 5, 6, 7, 8, 9, 10 or more outlets. In a particular embodiment, the fluid channel comprises a plurality of outlets distributed so that the fluid which exits the fluid channel through each outlet corresponds to fluid within a certain region around the primary axis. An advantage of this may be, that the fluid which exits the fluid channel through a particular outlet, corresponds to a particular layer of liquid within a certain region around the primary axis which may comprises sorted microscopic objects, such as microscopic objects of a particular category, as determined by the detection system. An advantage of this embodiment may thus be, that it enables sorting microscopic objects by allowing microscopic objects being displaced to a certain position along the primary axis to flow out of the fluid channel through a specific outlet.

According to another embodiment, there is provided a system, wherein the fluid channel is dimensioned so as to enable hydrodynamic focusing and/or hydrodynamic defocusing. By hydrodynamic focusing/defocusing is understood the process of changing the cross-section, such as changing the area of the cross-section and or the shape of the cross-section, of the fluid channel with the position along the flow, so as to increase or decrease a concentration of microscopic objects along the two geometric axes being orthogonal to the flow direction. In a particular embodiment, the hydrodynamic focusing serves to spread out the microscopic objects in a thin layer being parallel with the flow and orthogonal to the EMR beams. In a specific embodiment, the hydrodynamic (de-)focusing involves using a number, such as one or two of outer fluidic flows ("sheath flows") on one or more sides of a central sample flow so as to constrain the sample flow in one or more directions being orthogonal to a flow direction.

According to a second aspect, the invention further relates to a method for sorting microscopic objects comprising:
  Providing a laminar flow of fluid in a fluid channel comprising an inlet and an outlet, wherein the fluid comprises one or more microscopic objects,
  Determining a set of one or more positions of the one or more microscopic objects in the fluid channel,
  Providing a plurality of EMR beams being independently spatially controllable and propagating into the fluid channel, and
  Controlling the plurality of EMR beams based on the set of one or more positions, so as to enable each of the EMR beams in the plurality of EMR beams to exert a force on a microscopic object within the one or more microscopic objects,
  wherein the force has a direction having a component being parallel with a primary axis, wherein the primary axis is parallel with the EMR beam and orthogonal to a direction the flow of fluid, so as to enable sorting of the microscopic objects, such as sorting the microscopic objects, by displacing them spatially along the primary axis.

In a further embodiment, the microscopic particles are sorted by allowing the laminar flow of fluid to carry the microscopic objects into a plurality of outlets distributed along the primary axis. An advantage of this may be that it provides a relatively simple, yet efficient, method for sorting, such as separating, the microscopic objects, since they are simply led into the outlet corresponding to their position along the primary axis. The respective outlets may, e.g., lead towards various containers, such as a container for holding a purified sample with a specific type of microscopic objects, or waste outlets.

This aspect of the invention is particularly, but not exclusively, advantageous in that the method according to the present invention may be implemented by a system according to the first aspect. In a particular embodiment, the determining a set of one or more positions of the one or more microscopic objects in the fluid channel, such as said determining and controlling of the plurality of EMR beams is carried out on a timescale being smaller than, such as substantially smaller than a period of time wherein the microscopic objects would be pulled to the bottom or the top of the fluid channel under influence of gravitation or buoyancy. An advantage of carrying out the determining, such as the determining and controlling, relatively fast, may be that it speeds up the sorting. Another advantage may be that it enables sorting of the microscopic objects while suspended, i.e., the microscopic objects will not suffer from contact with the walls of the fluid channel or extensive contact with other microscopic objects. Another potential advantage may be, that it enables keeping all microscopic objects suspended in the fluid channel, i.e., both the microscopic objects of interest, and the remaining microscopic objects, which may then all be removed from the fluid channel immediately after the sorting process by means of the EMR beams, such as enabling removing all microscopic objects from the fluid channel simultaneously.

According to a second aspect, the invention further relates to use of a system according to the first aspect for sorting microscopic objects. A specific application may be sorting, such as isolation of, tumour cells in blood (also known as Circulating Tumor Cells (CTCs), which may be larger and/or have different morphological characteristics with respect to normal cells found in the blood). Another specific application may be sorting, such as isolation of very rare fetus cells from a pregnant woman's blood. Yet another specific application may be as a system for making a secondary sorting, after another system has made a primary sorting. This may in particular be relevant where another system may carry out a sorting, such as a mechanical sorting in a very fast, albeit not very specific manner.

In terms of capacity of the system, the sorting capacity may be calculated as follows. A "catapult speed" (i.e., the speed of the microscopic objects when moved with the scattering force) may be given by 800 microns/second, such as by using Matched filtering GPC (mGPC). The minimum distance we need to move the microscopic objects along the primary axis in order to separate them may be given by 50 microns. The number of objects which can be moved at once within the field of view (FoV) and the number of microscopic objects that are deliberately not moved are considered as the events/second. With FoV of 1×1 milimeter and microscopic objects (e.g., 5-10 micron in size) rather densely packed (e.g., by hydrodynamic focusing), e.g., each occupying a footprint of 10×10 square microns and assuming a 50-50 distribution and by using mGPC to maintain a narrow point-spread function for this FoV it is potentially possible to obtain a capacity of:

(800 micron/second/50 micron)×100×100=160.000 events/second

The number of microscopic objects which are in fact moved by the EMR beams corresponds to half of the above number in the above example. The number will be dramatically scaled up by the square factor implicitly given by the FoV area factor so that it can potentially reach a million events per second for a 2.5×2.5 square millimeters FOV.

In a particular embodiment, the capacity of the system is at least 1.000 events per second, such as at least 5.000 events per second, such as at least 10.000 events per second, such as at least 20.000 events per second, such as at least 30.000 events per second, such as at least 40.000 events per second, such as at least 50.000 events per second, at least 60.000 events per second, such as at least 70.000 events per second, such as at least 80.000 events per second, such as at least 90.000 events per second, such as at least 100.000 events per second, such as at least 160.000 events per second, such as at least 250.000 events per second, such as at least 500.000 events per second, such as at least 1.000.000 events per second.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The system, method and use according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
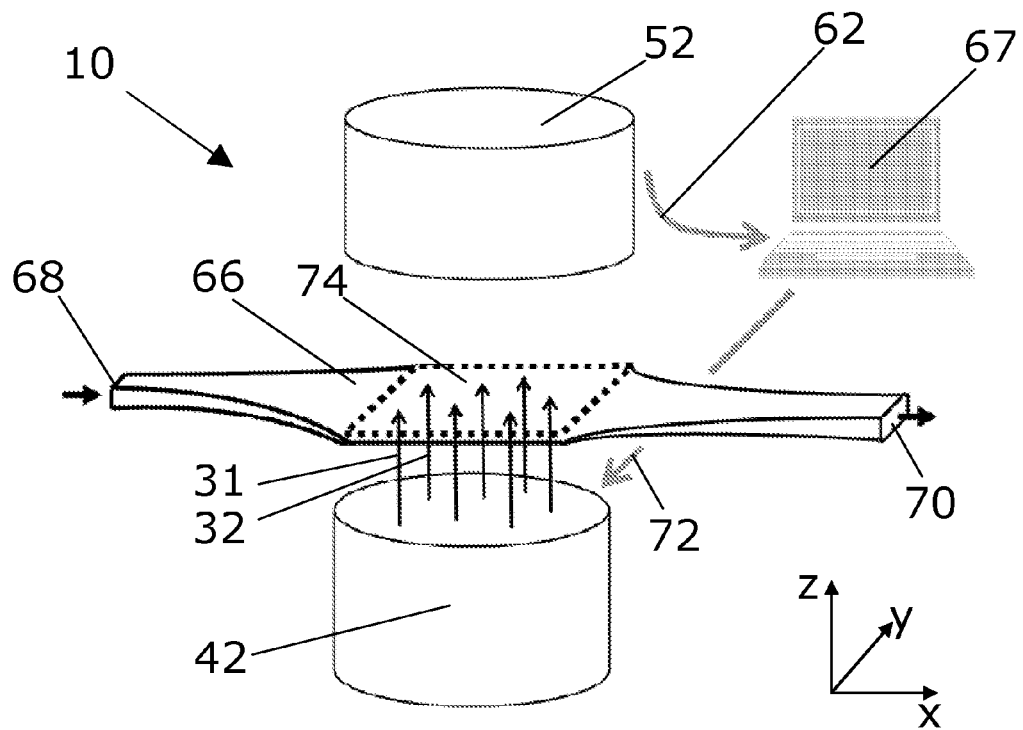
FIG. 1 shows a system for sorting microscopic objects.

FIG. 1 shows a system 10 for sorting microscopic objects 76, 78, 80 comprising:
  a fluid channel 66 comprising an inlet 68 and an outlet 70, the fluid channel being dimensioned so as to allow a flow of fluid between the inlet and the outlet to be laminar,
  a detection system 52 for determining a set of one or more positions of one or more microscopic objects in the fluid channel,
  means 42 for providing a plurality of EMR beams 31, 32 being independently spatially controllable and propagating into the fluid channel, and
  a controller 67, such as a processor or a computer, arranged for
    obtaining the set of one or more positions from the detection system 52 as indicated by arrow 62, and
    control the plurality of EMR beams 31, 32 based on the set of one or more positions, so as to enable each of the EMR beams in the plurality of EMR beams to exert a force on a microscopic object within the one or more microscopic objects, such as sending instructions as indicated by arrow 62 to the means 42 for providing a plurality of EMR beams 31, 32 in order to control the spatial positions of the plurality of EMR beams 31, 32,
wherein the force has a direction having a component being parallel with a primary axis z, wherein the primary axis is parallel with the EMR beam and orthogonal to a direction x of the flow of fluid, so as to enable sorting of the microscopic objects by displacing them spatially along the primary axis z.

It is noted that the fluid channel 66 also comprises region 74 in which the microscopic objects are to be sorted, which region may be bounded by one or more transparent walls, such as windows. The coordinate system in the lower right corner of FIG. 1 shows three axes, namely the x-axis which in the present figure is horizontal left-right and directed to the right, the z-axis which is vertical up-down and directed upwards, and the y-axis which is in the plane of the paper note that FIG. 1 is a perspective drawing and directed into the paper. The primary axis is parallel with the z-axis, which is also parallel with a direction of propagation of the plurality of EMR beams 31, 32. The fluid flow is parallel with the x-axis, i.e., the fluid flows from left to right. Each of the beams within the plurality of EMR beams 31, 32 may exert a force, such as a net force, on a microscopic object, which force is parallel with the direction of propagation of the beam, i.e., directed in the z-direction. The fluid flow is in the x-direction, which in the present figure is orthogonal to the z-direction it is noted that the x- and z-directions need not necessarily be mathematically orthogonal to each other, however, they cannot be parallel. The detection system 52 may be a vision based system. The detection system 52 may determine the set of one or more positions of the one or more microscopic objects in the fluid channel based on the properties of the microscopic objects in the fluid channel, including but not being limited to their colour, fluorescence and/or morphology, such as size and/or shape.

Figure 2:
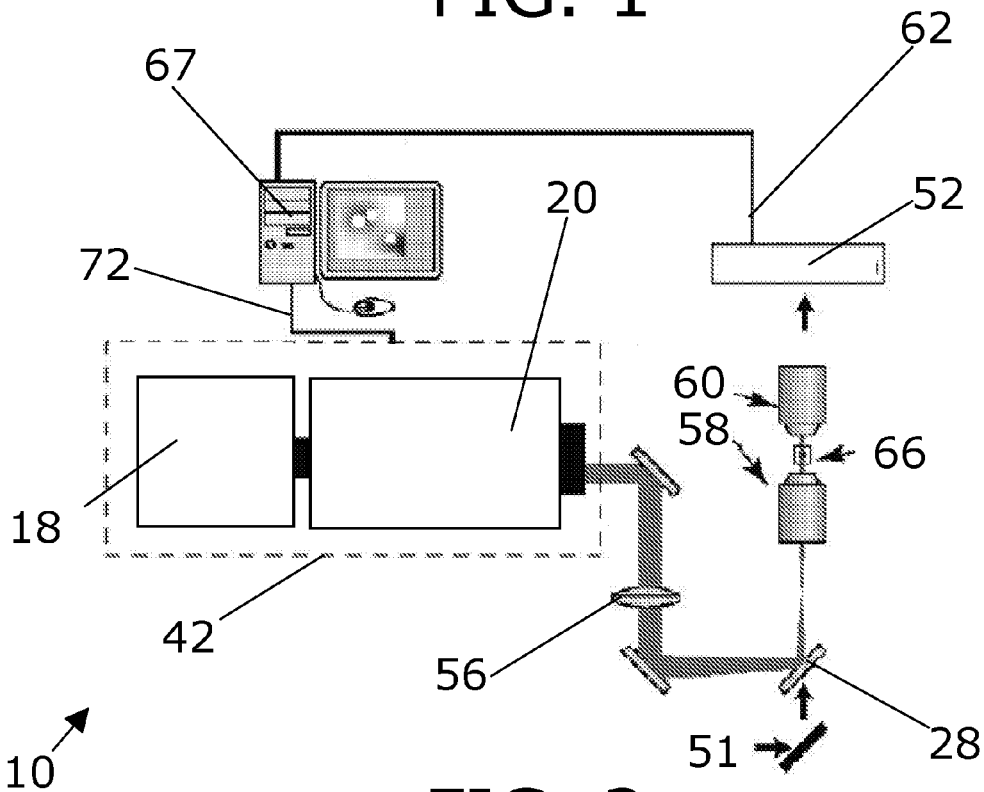
FIG. 2 shows the system of FIG. 1 with more details.

FIG. 2 shows the system 10 of FIG. 1 with more details regarding the means 42 for providing a plurality of EMR beams 31, 32. In particular, FIG. 2 shows means 42 for providing a plurality of EMR beams 31, 32 which further comprises a light source 18, which is a LASER light source, and a spatial light modulator 20 (SLM). The light source 18 emits light through the spatial light modulator 20 which modulates the light so as to provide a plurality of beams which may be directed to the fluid channel 66 via optical elements, such as via lens 56 and mirror 28. FIG. 2 furthermore shows that illumination light 51 may also be emitted through the fluid channel 66, so as to improve the capabilities of the detection system 52 in terms of obtaining the set of one or more positions of one or more microscopic objects in the fluid channel 66. In a particular embodiment, the detection means may employ a stereoscopic imaging system, such as an imaging system which enables providing 3D information regarding the positions of the microscopic objects in the flow channel by providing at least two offset images separately. The EMR beams as well as the illumination light may be transmitted via a lower objective 58 to the fluid channel, and an upper objective may further enhance the improve the capabilities of the detection system 52 in terms of obtaining the set of one or more positions of one or more microscopic objects in the fluid channel 66.

Figure 3:
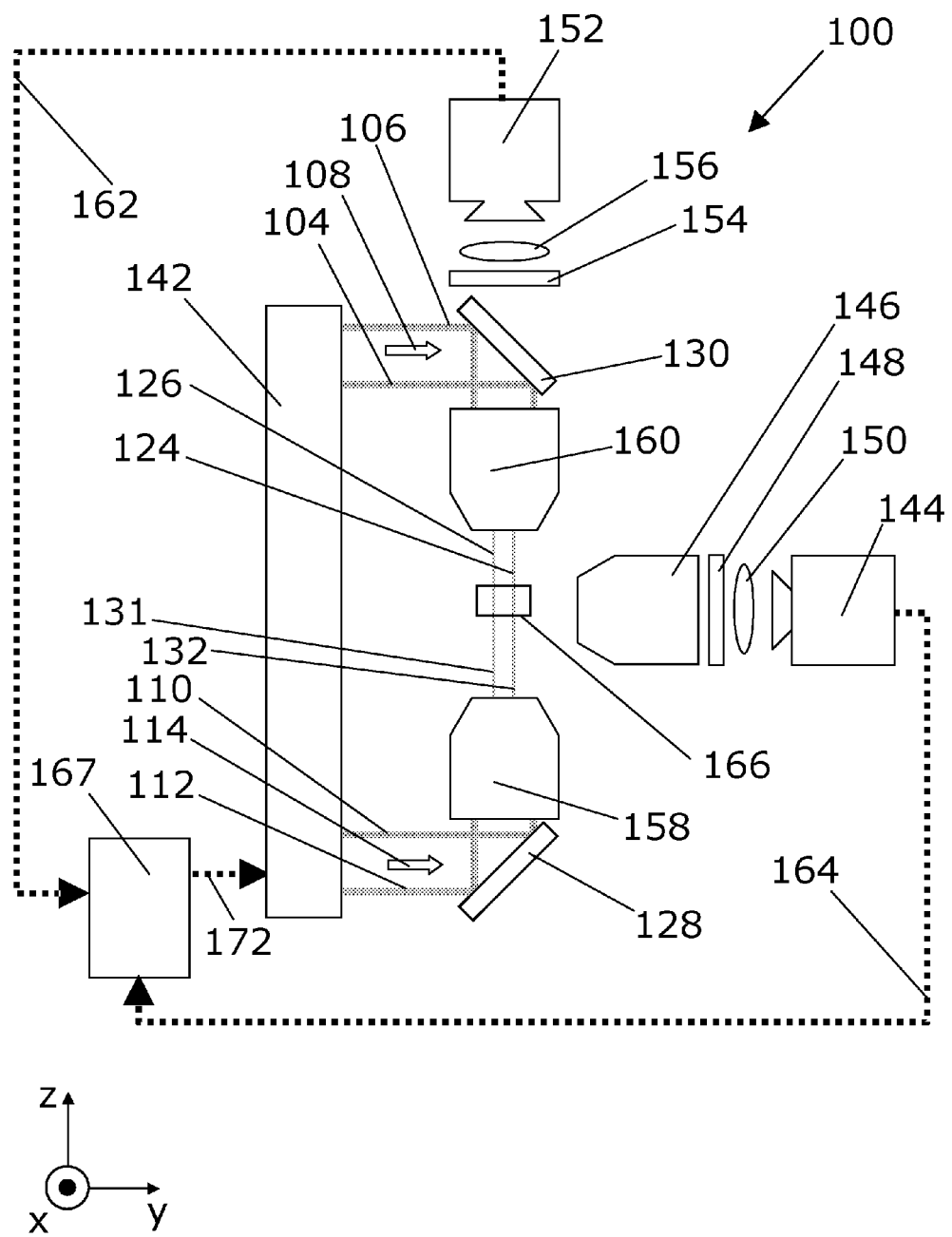
FIG. 3 shows another example of a system for sorting microscopic objects.

FIG. 3 shows another example of a system 100 for sorting microscopic objects 76, 78, 80. In more detail, the system 100 comprises means 142 for providing a plurality of EMR beams being independently spatially controllable and propagating into the fluid channel 166, wherein the means comprises a light source which emits one or more lower light beams 110, 112. The lower light beams have a lower direction 114 towards a lower dichroic mirror 128 which reflects the lower light beams 110, 112 into a lower microscope objective 158 so as to direct the lower light beams 130, 132 into a fluid channel 166. The means 142 for providing a plurality of EMR beams furthermore emits one or more upper light beams 104, 106 having an upper direction 108 towards an upper dichroic mirror 130 which reflects the upper light beams 104, 106 into an upper microscope objective 160 so as to direct the upper light beams 124, 126 into the fluid channel 166. The spatial position, shape and intensity of any one of the light beams may be controlled, such as controlled via one or more SLM's and/or adjustable optical elements, such as adjustable mirrors (not shown). In a particular embodiment, the upper and lower light beams may be controlled such as to form a setup for trapping one or more microscopic objects by using counter propagating beams. However, the upper and lower beams may also be controlled independently of each other. A possible advantage of having both upper and lower beams, potentially independently controllable, may be that it enables using the scattering force, i.e., light pressure in two directions, such as up and down, i.e., it enables moving microscopic objects in the positive z-direction and in the negative z-direction. The light source may be a LASER source emitting at 1064 nm. It is understood that the means 142 for providing a plurality of EMR beams may comprise one or more spatial light modulators (not shown) which receives light from the light source, and generates modified light arranged for exerting (scattering) forces on the plurality of microscopic objects. In a particular embodiment, the means 142 for providing a plurality of EMR beams being independently spatially controllable and propagating into the fluid channel may be embodied by the so-called BioPhotonics Workstation. The BioPhotonics Workstation is described in the reference "Independent trapping, manipulation and characterization by an all-optical biophotonics workstation", by H. U. Ulriksen et al., J. Europ. Opt. Soc. Rap. Public. 3, 08034 (2008) which is hereby incorporated in entirety by reference. The BioPhotonics Workstation uses near-infrared light ($\lambda$=1064 nm) from a fibre laser (IPG). Real-time spatial addressing of the expanded laser source in the beam modulation module produces reconfigurable intensity patterns. Optical mapping two independently addressable regions in a computer-controlled spatial light modulator as counter propagating beams in the sample volume enables trapping a plurality of micro-objects (currently generates up to 100 optical traps). The beams are relayed through opposite microscope objectives (Olympus LMPLN 50×IR, WD=6.0 mm, NA=0.55) into a 4.2 mm thick Hellma cell (250 µm×250 µm inner cross section). A user traps and steers the desired object(s) in three dimensions through a computer interface where the operator can select, trap, move and reorient cells and fabricated micro devices with a mouse or joystick in real-time. Videos of the experiments are grabbed simultaneously from the top-view and side-view microscopes. It is understood when referring to 'trap' or 'trapping' that trapping is a particular example in which scattering forces are applied, but where the scattering forces a balanced by other forces (which may also be scattering forces).

The particular setup depicted in FIG. 3 furthermore comprises a top camera 152 which may be useful for imaging via the upper microscope objective 160, the upper filter 154 and the upper lens 156 the fluid channel 166 from the top.

Similarly, the setup comprises a side camera 144 which may be useful for imaging via the side microscope objective 146, the side filter 148 and the side lens 150 the fluid channel 166 from the side. Having a plurality of cameras may be advantageous for improving the determination of a set of one or more positions of one or more microscopic objects in the fluid channel. Any one of the upper camera 152 and the side camera 144 may be a CCD camera, and may be connected to a controller 167 such as to enable visualizing or storing the obtained images, and/or for utilizing the images for guiding the means 142 for controlling the EMR beams 110, 112, 104, 108.

Furthermore, FIG. 3 shows a controller 167 arranged for obtaining the set of one or more positions from the detection system, such as using information gained via the cameras, and control the plurality of light beams based on the set of one or more positions, so as to enable each of the light beams in the plurality of EMR beams to exert a force on a microscopic object within the one or more microscopic objects in the fluid channel. The controller being a processor arranged for receiving information from sensing means, such as receiving upper view information 162 from the upper camera 152 and/or side view information 164 from side camera 144. The controller is further arranged for sending controlling information 172 to the means 142 for providing a plurality of EMR beams.

Figure 4:
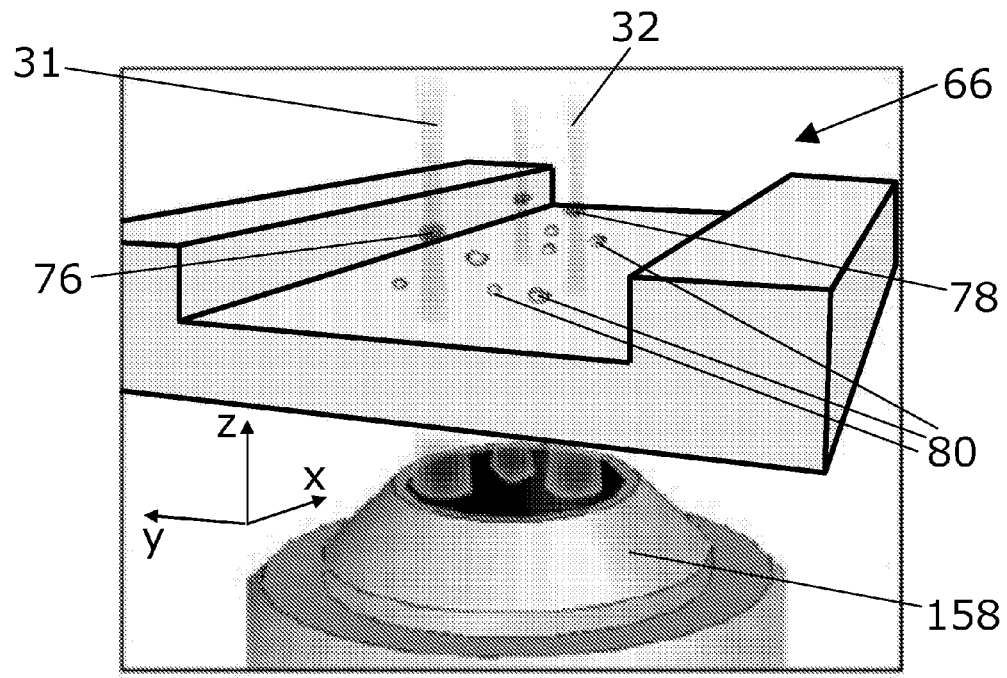
FIG. 4 shows a perspective view of the fluid channel (in a close up view)

FIG. 4 shows a perspective view of the fluid channel 66 (in a close up view) comprising microscopic objects 76, 78, 80. The fluid flows in the x-direction (into the plane of the paper), and the laser beams 31, 32 each have a direction upwards in the z-direction being orthogonal to the x-y-plane. However, the laser beams could also have had the opposite direction (downwards), or a direction being angled with respect to a direction being orthogonal to the x-y-plane-direction, such as being rotated around the y- and/or x-axis, such as rotated within 0-89 degrees with respect to a direction being orthogonal to the direction of the fluid flow, such as within 0-80 degrees, such as within 0-70 degrees, such as within 0-60 degrees, such as within 0-50 degrees, such as within 0-45 degrees, such as within 0-40 degrees, such as within 0-30 degrees, such as within 0-20 degrees, such as within 0-10 degrees, such as within 0-30 degrees, such as within 0-20 degrees, such as within 0-10 degrees, such as within 0-5 degrees, such as within 0-1 degrees. In FIG. 4, the detection system (not shown) has distinguished between at least two different categories of microscopic objects, namely between the light coloured microscopic objects, such as microscopic objects 80 and dark coloured microscopic objects, such as microscopic objects 76, 78, and has furthermore determined a set of one or more positions (such as a set comprising a number of corresponding x- and y-coordinates, such as number of corresponding x-, y-, and z-coordinates), comprising, such as consisting of, positions of microscopic objects 76, 78, as a category specific set of one or more positions of one or more microscopic objects of a specific category (i.e., dark coloured microscopic objects) in the fluid channel. In an alternative embodiment, the detection system may be arranged for distinguishing between at least two different categories of microscopic objects (such as light and dark coloured objects), and for determining a plurality of sets of one or more positions, such as a set corresponding to light coloured microscopic objects and another set corresponding to dark coloured microscopic objects, i.e., each set corresponding to a category specific set of one or more positions of one or more microscopic objects of a specific category in the fluid channel. In FIG. 4, the system which comprises the fluid channel is furthermore arranged so as to enable sorting of the microscopic objects within different categories by displacing them spatially along the primary axis according to their category. This is shown in the figure by having three independent laser beams, such as laser beams 31, 32, which are spatially moved in the x-y-plane so as to be incident on the microscopic objects to be sorted (such as isolated), such as one laser beam 31 being incident on microscopic object 76, and another laser beam 32 being incident on microscopic object 78. The scattering force of the incident light beam serves to impart a momentum to the respective microscopic objects, which will cause them to be accelerated in the direction of the incident light beam and gain velocity so as to move them in the direction of the incident light beam. Effectively, the microscopic objects 76,78 may be moved away from their initial position, and the microscopic objects of a certain category may thus be separated by moving them to a region along the z-coordinate which is substantially unique, such as unique for microscopic objects of that particular category.

Figure 5:
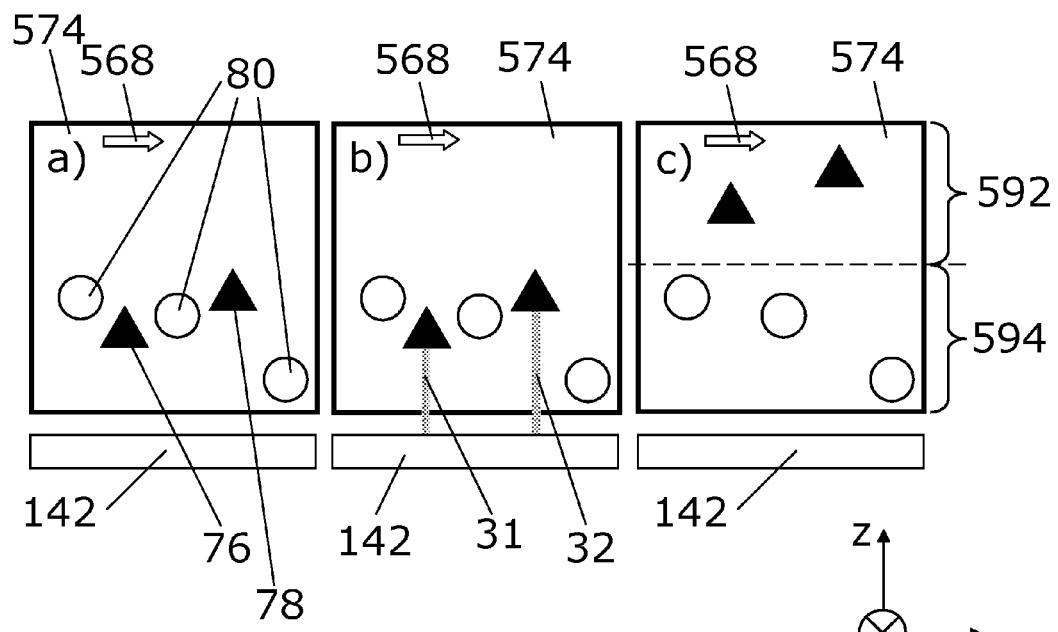
FIG. 5 represents a schematic illustration of a system.

FIG. 5 represents a schematic illustration of a system which is arranged so as to enable sorting of the microscopic objects within different categories by displacing them spatially along the primary axis according to their category.

FIG. 5A shows a part of a fluid channel and more specifically a region 574 in which the microscopic objects are to be sorted. The region 574 comprises microscopic objects 76, 78, 80 which belong to two different categories (such as one category comprising microscopic objects 76, 78 and another category comprising microscopic objects 80). The detection system is arranged for distinguishing between the two different categories of microscopic objects, and for determining a set of one or more positions, such as the position of microscopic objects 76, 78 as a category specific set of one or more positions of one or more microscopic objects of a specific category in the fluid channel. The direction of the flow in the fluid channel is indicated by arrow 568 and is from left to right, i.e., in the positive x-direction. In the present figure, the x-axis horizontal in a direction from left to right, the y-direction is horizontal in a direction into the plane of the paper, and the z-direction is vertical and is directed upwards (as indicated in the coordinate system in the figure). It is noted, that while the time-averaged flow rate is non-zero in order to transport the microscopic objects from left to right, the flow rate may at certain periods in time be reduced, such as completely stopped, so as to improve and/or simplify the task of the detection system of distinguishing between different categories of microscopic objects and/or determining positions. Similarly, the flow rate may at certain periods in time be reduced, such as completely stopped, so as to improve and/or simplify the task of the controller of controlling the plurality of EMR beams based on the set of one or more positions, so as to enable each of the EMR beams in the plurality of EMR beams to exert a force on a microscopic object within the one or more microscopic objects.

FIG. 5B shows a part of a fluid channel and more specifically a region 574 in which the microscopic objects are to be sorted wherein the controller (not shown) is controlling the plurality of EMR beams 31, 32 based on the set of one or more positions, so as to enable each of the EMR beams in the plurality of EMR beams to exert a force on a microscopic object, such as microscopic objects 76,78 identified in FIG. 5A as belonging to a specific category (to be sorted), within the one or more microscopic objects. The laser beams are emitted at spatially controlled position, such as spatially controlled in the x-y-plane, and emitted from the activation of the means 142 for providing a plurality of EMR beams. It is noted that the shown part of the fluid channel and more specifically a region 574 in which the microscopic objects are to be sorted, may (depending on the flow rate being zero or non-zero during a period between the determination of the positions and the activation of the means 142 for providing a plurality of EMR beams) be the same region 574 as in FIG. 5A (for a flow rate equalling zero) or it may be further downstream (for a flow rate being non-zero).

FIG. 5C shows the result of the activation of the means 142 for providing a plurality of EMR beams, namely that the radiation pressure, such as the scattering force from the laser beams 31, 32 in FIG. 5B has exerted a force on microscopic objects 76, 78 so as to move them from a lower part 594 of the region 574 to an upper part 592 of the region 574. Effectively, the microscopic objects have been sorted by placing them in distinct regions distributed along a primary axis, which in the present example is parallel with the z-axis.

Figure 6:
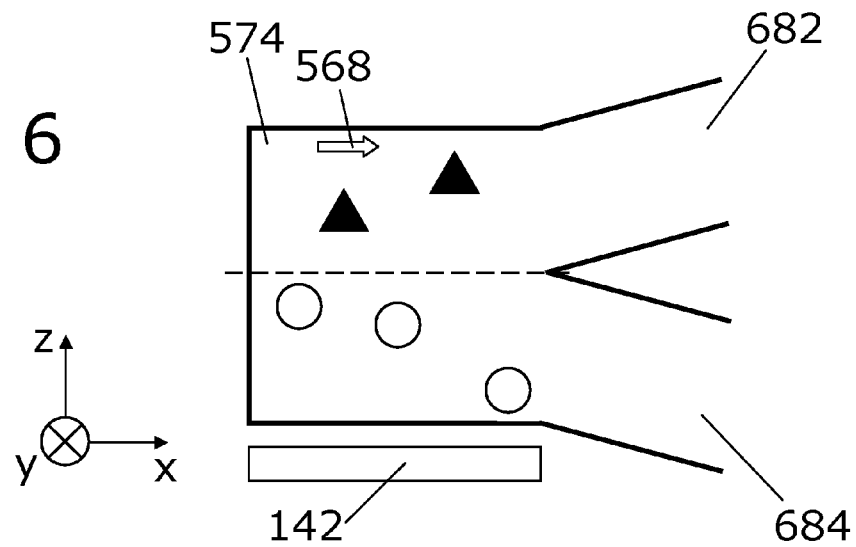
FIG. 6 shows a region, in which the microscopic objects are to be sorted.

FIG. 6 shows a region 574 in which the microscopic objects are to be sorted, which region 574 is similar to the region depicted in FIG. 5C, and also comprising similar microscopic objects at similar positions. Furthermore is shown in FIG. 6 a plurality of outlets distributed along the primary axis, more specifically two outlets, namely an upper outlet 682 and a lower outlet 684 being distributed along the z-axis.

Figure 7:
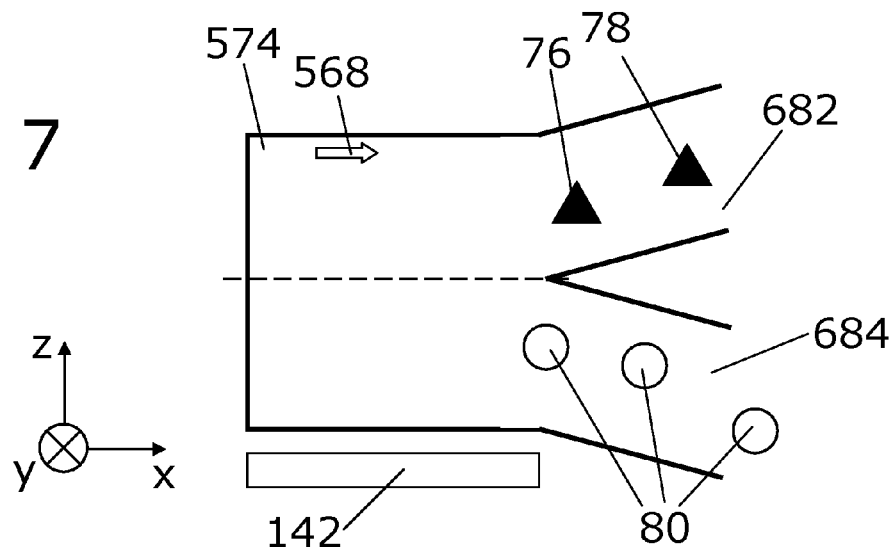
FIG. 7 shows a region, in which the microscopic objects are to be sorted.

FIG. 7 shows a region 574 in which the microscopic objects are to be sorted, which region 574 is similar to the region depicted in FIG. 6, however a period of time has passed between FIG. 6 and FIG. 7 in which there has been applied a non-zero flow rate so that the fluid has been flowing in a direction indicated by arrow 568, such that the microscopic objects have been transported from the region 574 and into the outlets 682, 684. More specifically, objects 76, 78 which have been deliberately displaced (cf., FIG. 5B-C) so as to be positioned in the upper part of the region 574 are exiting the region 574 via upper outlet 682, while the remaining microscopic objects 80 which were not displaced (cf., FIG. 5B-C) are exiting the region 574 via lower outlet 684. Hence, a sorting of the objects 76, 78 from the remaining objects 80 have been realized, and the objects 76, 80 may be collected at the end of the outlet 682, e.g., in a beaker or another container.

Figure 8:
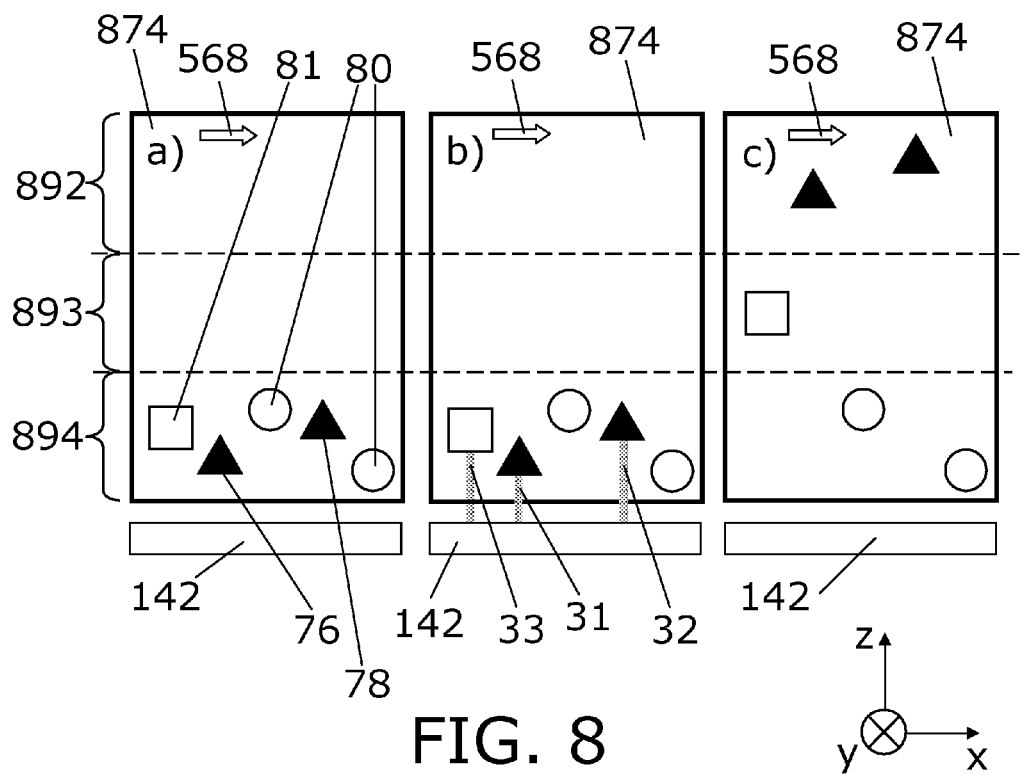
FIG. 8 represents a schematic illustration of a system.
Figure 9:
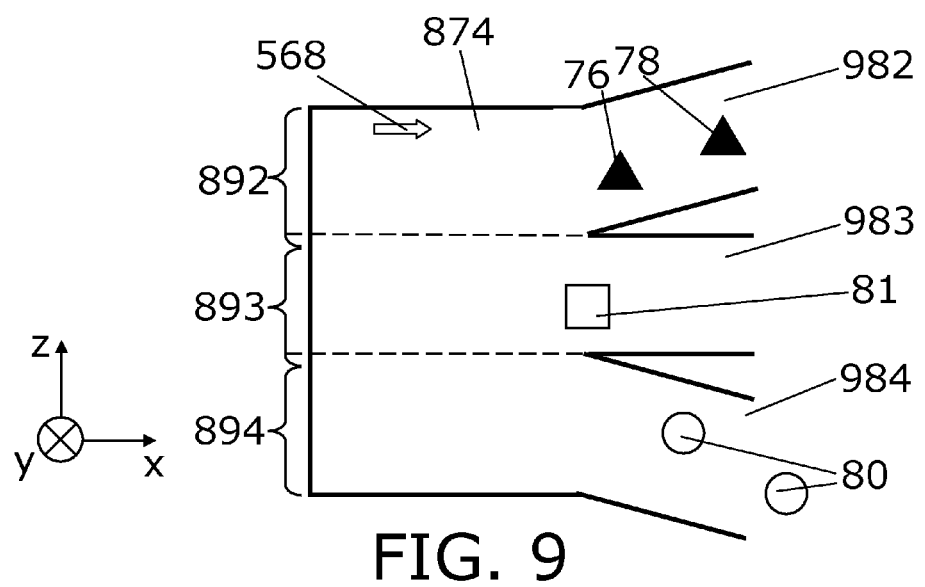
FIG. 9 shows a region, in which the microscopic objects are to be sorted.

FIGS. 8-9 show steps in a sorting method which is similar to the method outlined in FIGS. 5-7, although FIGS. 8-9 sort the microscopic objects into three different categories.

FIG. 8 represents a schematic illustration of a system which is arranged so as to enable sorting of the microscopic objects within three different categories by displacing them spatially along the primary axis according to their category.

FIG. 8A shows in analogy with FIG. 5A a part of a fluid channel and more specifically a region 874 in which the microscopic objects are to be sorted. However, in FIG. 8A there are three different categories of microscopic objects, namely a category which comprises microscopic objects 76, 78, another category comprising microscopic objects 80, and yet another category comprising microscopic object 81. The detection system (not shown) is arranged for distinguishing between the three different categories of microscopic objects, and for determining a plurality of sets of one or more positions, each corresponding to a category specific set of one or more positions of one or more microscopic objects of a specific category in the fluid channel.

FIG. 8B shows in analogy with FIG. 5B a part of a fluid channel and more specifically a region 874 in which the microscopic objects are to be sorted wherein the controller (not shown) is controlling the plurality of EMR beams 31, 32, 33 based on the set of one or more positions, so as to enable each of the EMR beams in the plurality of EMR beams to exert a force on a microscopic object, such as microscopic objects 76,78 identified in FIG. 8A as belonging to a specific category (to be sorted), within the one or more microscopic objects. In FIG. 8B the microscopic objects of the different are not all moved to the same region around the primary axis. For example, microscopic objects 76, 78 (see FIG. 8A) are imparted an impulse via the scattering force of laser beams 31, 32 so as to be moved into an upper region 892 within region 874, and microscopic object 81 is imparted an impulse via the scattering force of laser beam 33 so as to be moved into a middle region 893 within region 874. The remaining microscopic objects 80 stay in the lower region 894 within region 874. The laser beams may be controlled so as to move each microscopic object a predetermined distance, such as by controlling the intensity of the individual laser beams and/or the time the laser beam is applied.

FIG. 8C shows in analogy with FIG. 5C the result of the activation of the means 142 for providing a plurality of EMR beams, namely that the radiation pressure, such as the scattering force from the laser beams 31, 32, 33 in FIG. 8B has exerted a force on microscopic objects 76, 78 so as to move them from a lower part 894 of the region 874 to an upper part 892 of the region 874, and similarly move microscopic object 81 to a middle part 893 of region 874. Effectively, the microscopic objects have been sorted by placing them in distinct regions distributed along a primary axis, which in the present example is parallel with the z-axis.

FIG. 9 shows in analogy with FIG. 7 a region 874 in which the microscopic objects are to be sorted, which region 874 is similar to the region depicted in FIG. 8C. Furthermore is shown in FIG. 9 a plurality of outlets distributed along the primary axis, more specifically three outlets, namely an upper outlet 982, a middle outlet 983 and a lower outlet 984 being distributed along the z-axis. As in FIG. 7, the microscopic objects are sorted into specific outlets (such as outlet 982, outlet 983 or outlet 984) depending on their position with respect to the z-axis in the region 874. It is noticed that since there are three outlets, and since the controller is arranged for controlling the means 142 for providing a plurality of EMR beams 31, 32, 33 being independently spatially controllable and propagating into the fluid channel, and the laser beams being controlled so as to move the individual microscopic objects a predetermined individual distance, it may be possible to sort the microscopic objects according to three different categories. It is noticed that by having more outlets, it may be possible to extend this principle so as to be able to sort into a plurality of categories, such as 2, 3, 4, 5, 6, 7, 8, 9, 10 or more categories.

It is noted, that besides having different outlets, it may also be possible to sort microscopic objects by placing them at different positions with respect to the z-axis, and if the flow profile with respect to the z-axis is different, i.e., if the fluid flows faster at some positions than others, then differences in z-coordinate may translate into differences in x-coordinate. This may for instance be realistic if the flow profile is parabolic.

Figure 10:
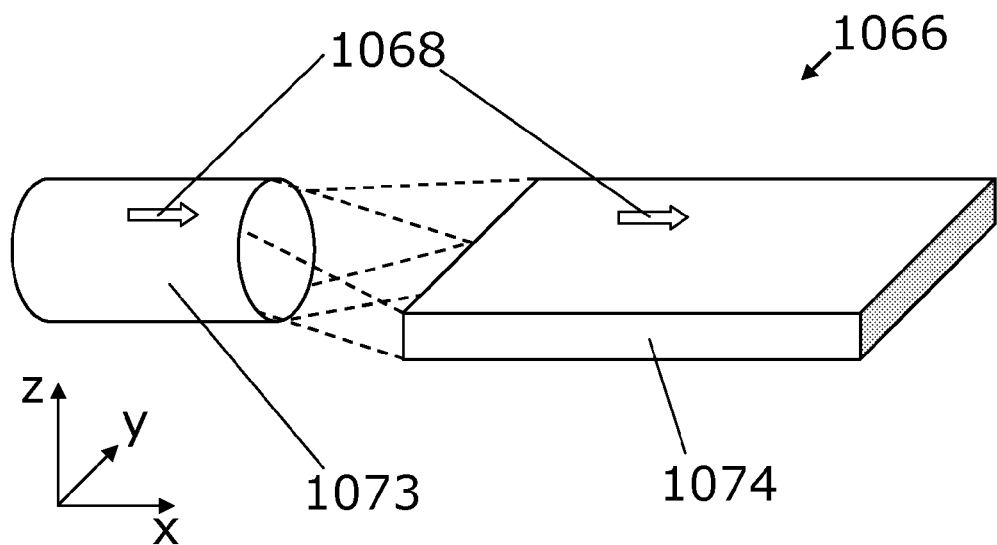
FIGS. 10-12 illustrate the principle of hydrodynamic focusing and defocusing.
Figure 11:
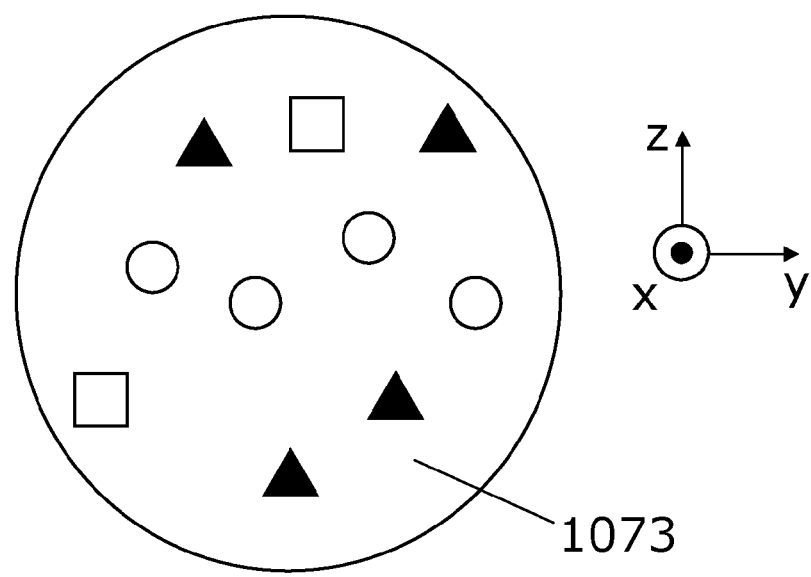
Figure 12:
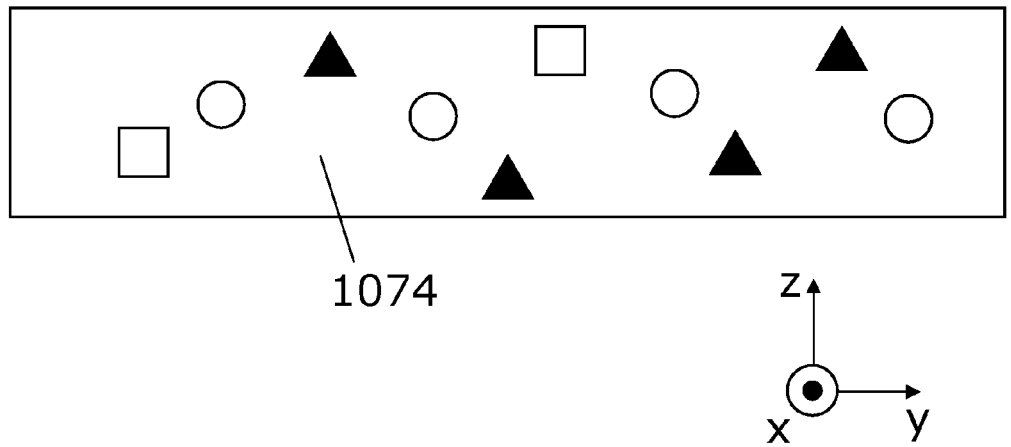

FIGS. 10-12 illustrate the principle of hydrodynamic focusing and defocusing.

FIG. 10 shows a fluid channel 1066 is dimensioned so as to enable hydrodynamic focusing and/or hydrodynamic defocusing. The first part 1073 of the fluid channel is a tubular element, with a circular cross-section, i.e., the cross-section in the y-z-plane, which is orthogonal to the flow direction in the x-direction as indicated by arrows 1068, is circular. However, downstream of the first part 1073 the cross section changes, so as to be rectangular in the region 1074. Thus, the fluid has been focused in the z-direction, but defocused in the y-direction.

FIG. 11 shows the cross-section of the first part 1073 of FIG. 10 in the y-z-plane.

FIG. 12 shows the cross-section of the downstream part 1074 of FIG. 10 in the y-z-plane.

In both of FIGS. 11-12, it is shown that microscopic objects are positioned within the cross-section, and it is furthermore shown that the focusing and defocusing serve to position the microscopic objects in a narrow region with respect to the z-axis, i.e., in a plane around a certain z-coordinate, and simultaneously the microscopic objects are spread out in the plane, so that larger distances between the microscopic objects with respect to the y-axis has been achieved. A possible advantage of this is that the individual microscopic objects may be easier to detect and examine for the detection system and may furthermore be easier to target, i.e., to illuminate with EMR beams for the means for providing a plurality of EMR beams being independently spatially controllable and propagating into the fluid channel and being incident upon one or more specific microscopic objects.

Figure 13:
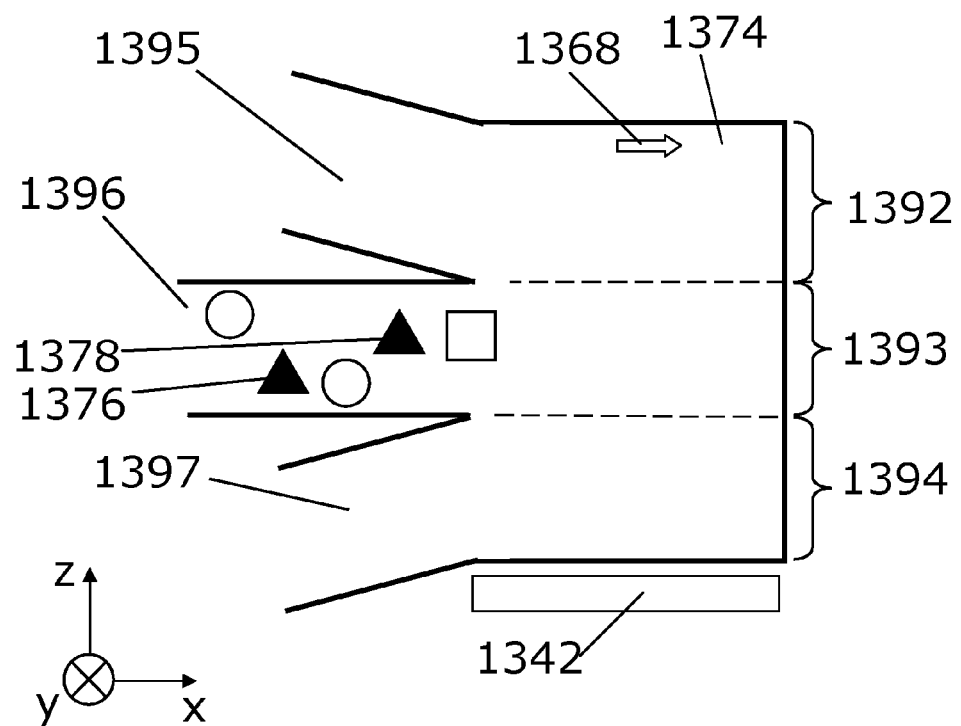
FIG. 13 shows another example of hydrodynamic focusing.

FIG. 13 shows another example of hydrodynamic focusing in which microscopic objects 1376, 1378 are comprised within a middle tubing 1396 entering into the region 1374, and furthermore an upper tubing 1395 and a lower tubing 1397 are entering into the region 1374. The flow is from left to right as indicated by arrow 1368. By controlling the flow rate of the flow of each tubing, the height (with respect to the z-axis of the layer 1393 (in which the microscopic objects originally located in the middle tubing will end up in) may be influenced by the relative flow rates of the fluid flows in the tubing 1395, 1396, 1397.

Figure 14:
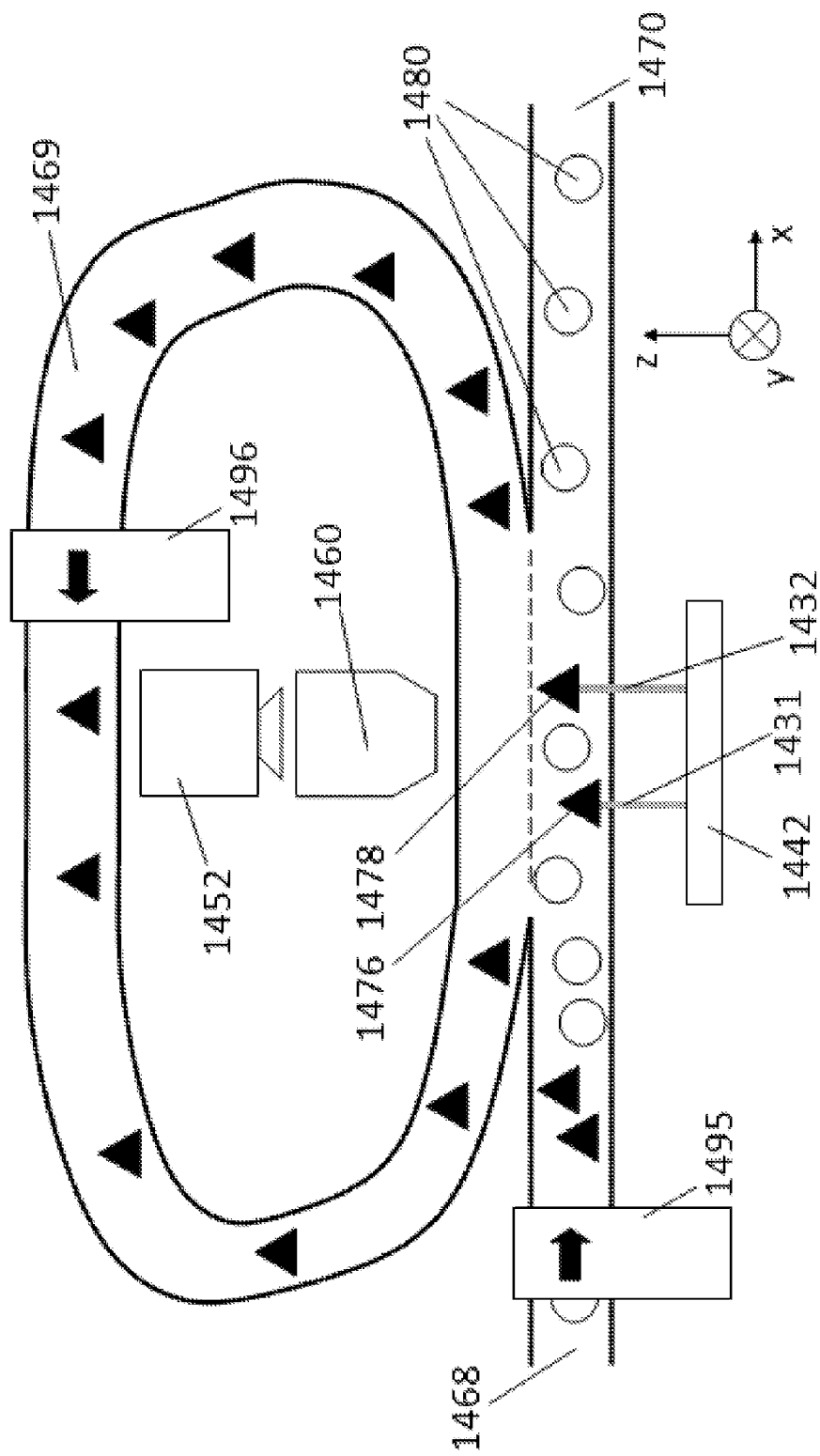
FIG. 14 shows an example of a loop for enabling recirculation of fluid.

FIG. 14 shows an example of a loop 1469 for enabling recirculation of fluid. An inlet 1468 allows fluid to enter the system and pump 1495 serves to draw fluid from the inlet and into the system. The fluid may comprise microscopic objects 1476, 1478, 1480. A detection system comprising a camera 1452 and an upper objective 1460 serves to identify positions of certain microscopic objects 1476, 1478, and means 1442 for providing a plurality of EMR beams 31, 32 being independently spatially controllable and propagating into the fluid channel serves to move those microscopic objects into the loop. Another pump 1469 serves to recirculate the fluid in the loop. Fluid may exit the system via outlet 1470. By having a loop a continuously increasing concentration of microscopic objects of a certain category in the loop may be achieved. Another potential advantage may be that the detection system may continuously monitor the microscopic objects in the loop, so as to continuously verify that only those microscopic objects belonging to that category are present in the loop. In a particular embodiment, means (not shown) for providing a plurality of EMR beams being independently spatially controllable and propagating into the fluid channel in the opposite direction of the means 142 (i.e., in the negative z-direction, i.e., downwards) may be utilized for removing microscopic objects from the loop.

In a particular embodiment, there is provided a system 10 for sorting microscopic objects 76, 78, 80 comprising:
  a fluid channel 66 comprising an inlet 68 and an outlet 70, the fluid channel being dimensioned so as to allow a flow of fluid between the inlet and the outlet to be laminar,
  a detection system 52 for determining a set of one or more positions of one or more microscopic objects in the fluid channel,
  means 42 for providing a plurality of EMR beams 31, 32 being independently spatially controllable and propagating into the fluid channel, and
  a controller 67, such as a processor or a computer, arranged for
    obtaining the set of one or more positions from the detection system 52 as indicated by arrow 62, and
    control the plurality of EMR beams 31, 32 based on the set of one or more positions, so as to enable each of the EMR beams in the plurality of EMR beams to exert a force on a microscopic object within the one or more microscopic objects, such as sending instructions as indicated by arrow 62 to the means 42 for providing a plurality of EMR beams 31, 32 in order to control the spatial positions of the plurality of EMR beams 31, 32,
wherein the force has a direction having a component being parallel with a primary axis z, wherein the primary axis is parallel with the EMR beam and orthogonal to a direction x of the flow of fluid, so as to enable sorting of the microscopic objects by displacing them spatially along the primary axis z.

To sum up, there is presented a system 10, 100 for sorting microscopic objects 76, 78, 80, where the system comprises a fluid channel 66 with an inlet 68 and an outlet 70, where the fluid channel is arranged for allowing the fluid flow to be laminar. The system furthermore comprises a detection system 52 which enables detecting microscopic objects in the fluid channel and furthermore enables determining their position. The system furthermore comprises a controller 67, such as a computer, which receives the positions and accordingly controls a source of light beams so as to "shoot" light beams towards selected microscopic objects so as to "push" them into a new position. The system thereby enables sorting the selected microscopic objects. In more specific embodiments, the detection system furthermore assigns different categories to different microscopic objects, so as to enable sorting based on multiple categories.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

In exemplary embodiments E1-E15, the invention may relate to:
  E1. A system (10, 100) for sorting microscopic objects (76, 78, 80) comprising:
    a fluid channel (66) comprising an inlet (68) and an outlet (70), the fluid channel being dimensioned so as to allow a flow of fluid between the inlet and the outlet to be laminar,
    a detection system (52) for determining a set of one or more positions of one or more microscopic objects in the fluid channel, wherein the detection system is arranged for determining the set of one or more positions of one or more microscopic objects being suspended in the fluid channel,
    means (42) for providing a plurality of electromagnetic radiation beams (31, 32) being independently spatially controllable and propagating into the fluid channel, and
    a controller (67) arranged for
      obtaining the set of one or more positions from the detection system (52), and
      control the plurality of electromagnetic radiation beams (31, 32) based on the set of one or more positions, so as to enable each of the electromagnetic radiation beams in the plurality of electromagnetic radiation beams to exert a force on a microscopic object within the one or more microscopic objects,
    wherein the force has a direction having a component being parallel with a primary axis (z), wherein the primary axis is parallel with the electromagnetic radiation beam and orthogonal to a direction (x) of the flow of fluid, so as to enable sorting of the microscopic objects by displacing them spatially along the primary axis (z).

E2. A system according to embodiment E1, wherein the fluid channel is dimensioned so that a flow of pure water at room temperature may have a Reynolds number below 4000.

E3. A system according to embodiment E1, wherein the means for providing a plurality of electromagnetic radiation beams comprises any one of: A Generalized Phase Contrast setup and diffractive optics.

E4. A system according to embodiment E1, wherein the detection system is arranged for distinguishing between at least two different categories of microscopic objects, and for determining the set of one or more positions as a category specific set of one or more positions of one or more microscopic objects of a specific category in the fluid channel.

E5. A system according to embodiment E1, wherein the detection system is arranged for distinguishing between at least two different categories of microscopic objects, and for determining a plurality of sets of one or more positions, each corresponding to a category specific set of one or more positions of one or more microscopic objects of a specific category in the fluid channel.

E6. A system according to any one of embodiments E4 or E5, wherein the system is arranged so as to enable sorting of the microscopic objects within different categories by displacing them spatially along the primary axis according to their category.

E7. A system according to embodiment E1, wherein the system comprises a loop for enabling recirculation of the fluid.

E8. A system according to embodiment E1, wherein each of the electromagnetic radiation beams within the plurality of electromagnetic radiation beams is non-divergent.

E9. A system according to embodiment E1, wherein the controller (67) is arranged for controlling the plurality of electromagnetic radiation beams (31, 32) based on the set of one or more positions, so as to enable each of the electromagnetic radiation beams in the plurality of electromagnetic radiation beams to exert a force on a microscopic object within the one or more microscopic objects, while the microscopic objects are suspended in the fluid channel (66).

E10. A system according to embodiment E1, wherein the system furthermore comprises a pumping system for driving the fluid through the fluid channel.

E11. A system according to embodiment E11, wherein the pumping system is arranged for stopping and starting the flow depending on an operational status of the detection system and/or the controller.

E12. A system according to embodiment E1, wherein the fluid channel comprises a plurality of outlets distributed along the primary axis.

E13. A system according to embodiment E1, wherein the fluid channel is dimensioned so as to enable hydrodynamic focusing and/or hydrodynamic defocusing.

E14. A method for sorting microscopic objects comprising:
Providing a laminar flow of fluid in a fluid channel comprising an inlet and an outlet, wherein the fluid comprises one or more microscopic objects,
Determining a set of one or more positions of the one or more microscopic objects in the fluid channel,
Providing a plurality of electromagnetic radiation beams being independently spatially controllable and propagating into the fluid channel, and
Controlling the plurality of electromagnetic radiation beams based on the set of one or more positions, so as to enable each of the electromagnetic radiation beams in the plurality of electromagnetic radiation beams to exert a force on a microscopic object within the one or more microscopic objects,
wherein the force has a direction having a component being parallel with a primary axis, wherein the primary axis is parallel with the electromagnetic radiation beam and orthogonal to a direction (x) of the flow of fluid, so as to enable sorting of the microscopic objects by displacing them spatially along the primary axis.

E15. Use of a system according to any one of embodiments E1-E13 for sorting microscopic objects.

The invention claimed is:

1. A system for sorting microscopic objects comprising:
a fluid channel comprising an inlet and an outlet, the fluid channel being dimensioned so as to allow a flow of fluid between the inlet and the outlet to be laminar,
a detection system for determining a set of one or more positions of one or more microscopic objects in the fluid channel, wherein the detection system is arranged for determining the set of one or more positions of one or more microscopic objects being suspended in the fluid channel,
an electromagnetic radiation source for providing a plurality of electromagnetic radiation beams being independently spatially controllable and propagating into the fluid channel, and
a controller arranged for:
obtaining the set of one or more positions from the detection system, and
controlling the plurality of electromagnetic radiation beams based on the set of one or more positions, so as to enable each of the electromagnetic radiation beams in the plurality of electromagnetic radiation beams to exert a force on a microscopic object within the one or more microscopic objects while the microscopic objects are suspended in the fluid channel,
wherein the force has a direction having a component being parallel with a primary axis, wherein the primary axis is parallel with the electromagnetic radiation beam and orthogonal to a direction of the flow of fluid, so as to enable sorting of the microscopic objects by displacing them spatially along the primary axis,
wherein each of the electromagnetic radiation beams within the plurality of electromagnetic radiation beams is not being focused to a degree enabling three-dimensional trapping of microscopic objects within the fluid channel and wherein the fluid channel comprises a plurality of outlets distributed along the primary axis.

2. The system according to claim 1, wherein the force is a scattering force.

3. The system according to claim 1, wherein the electromagnetic radiation source is configured to provide a plurality of upper and lower electromagnetic radiation beams, wherein the upper and lower electromagnetic radiation beams are arranged so as to form counter propagating beams which may be controlled so as to exert the force on the microscopic objects.

4. The system according to claim 3, wherein the system is arranged so as to enable sorting of the microscopic objects within different categories by displacing them spatially along the primary axis according to their category.

5. The system according to claim 1, wherein the fluid channel is dimensioned so that a flow of pure water at room temperature may have a Reynolds number below 4000.

6. The system according to claim 1, wherein the electromagnetic radiation source comprises a Generalized Phase Contrast setup and/or diffractive optics.

7. The system according to claim 1, wherein the detection system is arranged for distinguishing between at least two different categories of microscopic objects, and for determining the set of one or more positions as a category specific set of one or more positions of one or more microscopic objects of a specific category in the fluid channel.

8. The system according to claim 1, wherein the detection system is arranged for distinguishing between at least two different categories of microscopic objects, and for determining a plurality of sets of one or more positions, each corresponding to a category specific set of one or more positions of one or more microscopic objects of a specific category in the fluid channel.

9. The system according to claim 1, wherein the system comprises a loop for enabling recirculation of the fluid.

10. The system according to claim 1, wherein each of the electromagnetic radiation beams within the plurality of electromagnetic radiation beams is non-divergent.

11. The system according to claim 1, wherein the system furthermore comprises a pumping system for driving the fluid through the fluid channel.

12. The system according to claim 11, wherein the pumping system is arranged for stopping and starting the flow depending on an operational status of the detection system and/or the controller.

13. The system according to claim 1, wherein the fluid channel is dimensioned so as to enable hydrodynamic focusing and/or hydrodynamic defocusing.

14. A method for sorting microscopic objects comprising:
providing a laminar flow of fluid in a fluid channel comprising an inlet and an outlet, wherein the fluid comprises one or more microscopic objects,
determining a set of one or more positions of the one or more microscopic objects in the fluid channel,
providing a plurality of electromagnetic radiation beams being independently spatially controllable and propagating into the fluid channel, and
controlling the plurality of electromagnetic radiation beams based on the set of one or more positions, so as to enable each of the electromagnetic radiation beams in the plurality of electromagnetic radiation beams to exert a force on a microscopic object within the one or more microscopic objects while the microscopic objects are suspended in the fluid channel,
wherein the force has a direction having a component being parallel with a primary axis, wherein the primary axis is parallel with the electromagnetic radiation beam and orthogonal to a direction of the flow of fluid, so as to enable sorting of the microscopic objects, or sorting the microscopic objects, by displacing them spatially along the primary axis,
wherein each of the electromagnetic radiation beams within the plurality of electromagnetic radiation beams is not being focused to a degree enabling three-dimensional trapping of microscopic objects within the fluid channel and wherein the fluid channel comprises a plurality of outlets distributed along the primary axis.

* * * * *